(12) United States Patent
Chana et al.

(10) Patent No.: US 9,700,328 B2
(45) Date of Patent: Jul. 11, 2017

(54) REMOVAL OF ARTICLES EMBEDDED IN SURROUNDING MATERIAL

(75) Inventors: Gursharan Singh Chana, Sutton Coldfield (GB); Shaun Palmer, Sheffield (GB)

(73) Assignee: Comis Orthopaedics Limited (GB)

( * ) Notice: Subject to any disclaimer, the term of this patent is extended or adjusted under 35 U.S.C. 154(b) by 935 days.

(21) Appl. No.: 13/502,071

(22) PCT Filed: Oct. 14, 2010
(Under 37 CFR 1.47)

(86) PCT No.: PCT/GB2010/001909
§ 371 (c)(1),
(2), (4) Date: Aug. 27, 2013

(87) PCT Pub. No.: WO2011/045568
PCT Pub. Date: Apr. 21, 2011

(65) Prior Publication Data
US 2014/0135781 A1    May 15, 2014

Related U.S. Application Data

(60) Provisional application No. 61/251,842, filed on Oct. 15, 2009.

(30) Foreign Application Priority Data

Oct. 14, 2009    (GB) .................................. 0918006.8

(51) Int. Cl.
*A61B 17/58*    (2006.01)
*A61B 17/60*    (2006.01)
(Continued)

(52) U.S. Cl.
CPC ........ *A61B 17/1739* (2013.01); *A61F 2/4603* (2013.01); *B23B 47/28* (2013.01);
(Continued)

(58) Field of Classification Search
None
See application file for complete search history.

(56) References Cited

U.S. PATENT DOCUMENTS

| 4,399,813 A | 8/1983 | Barber |
| 5,190,551 A | 3/1993 | Chin et al. |

(Continued)

FOREIGN PATENT DOCUMENTS

| DE | 29609811 U1 | 8/1996 |
| EP | 1205150 A2 | 5/2002 |

(Continued)

OTHER PUBLICATIONS (Australian Patent Application No. 2010308165) IP Australia, Patent Examination Report.

(Continued)

*Primary Examiner* — Sameh Boles
(74) *Attorney, Agent, or Firm* — Ice Miller LLP

(57) ABSTRACT

A drill guide comprises a mounting arrangement for mounting the drill guide on an article. The drill guide further includes first and second guide arrangements and a holding arrangement for holding the first and second drill guides. The holding arrangement is adjustable between a release position in which the positions of the first and second guide arrangements are adjustable relative to the holding arrangement and a holding position in which the first and second guide arrangements are held by the holding arrangement in a fixed position.

25 Claims, 32 Drawing Sheets

(51) Int. Cl.
    *A61F 2/00*      (2006.01)
    *A61B 17/17*      (2006.01)
    *A61F 2/46*      (2006.01)
    *B23B 47/28*      (2006.01)
    *A61B 17/92*      (2006.01)

(52) U.S. Cl.
    CPC .......... *A61B 17/175* (2013.01); *A61B 17/921* (2013.01); *A61F 2002/4619* (2013.01); *A61F 2002/4627* (2013.01); *A61F 2002/4628* (2013.01)

(56) References Cited

U.S. PATENT DOCUMENTS

| | | | |
|---|---|---|---|
| 5,290,291 | A | 3/1994 | Linden |
| 5,676,500 | A | 10/1997 | Sommerfeld |
| 2010/0121339 | A1* | 5/2010 | Whittaker .......... A61B 17/1714 606/98 |

FOREIGN PATENT DOCUMENTS

| | | | |
|---|---|---|---|
| EP | 1862243 | A2 | 12/2007 |
| FR | 2587196 | A1 | 3/1987 |
| WO | WO03105659 | A2 | 12/2003 |
| WO | WO2006091625 | A2 | 8/2006 |
| WO | WO2009027642 | A1 | 3/2009 |

OTHER PUBLICATIONS

PCT/GB2010/0019 International Searching Authority, International Search Report, May 17, 2011.
PCT/GB2010/0019 International Searching Authority, Written Opinion of the International Searching Authority, May 17, 2011.

\* cited by examiner

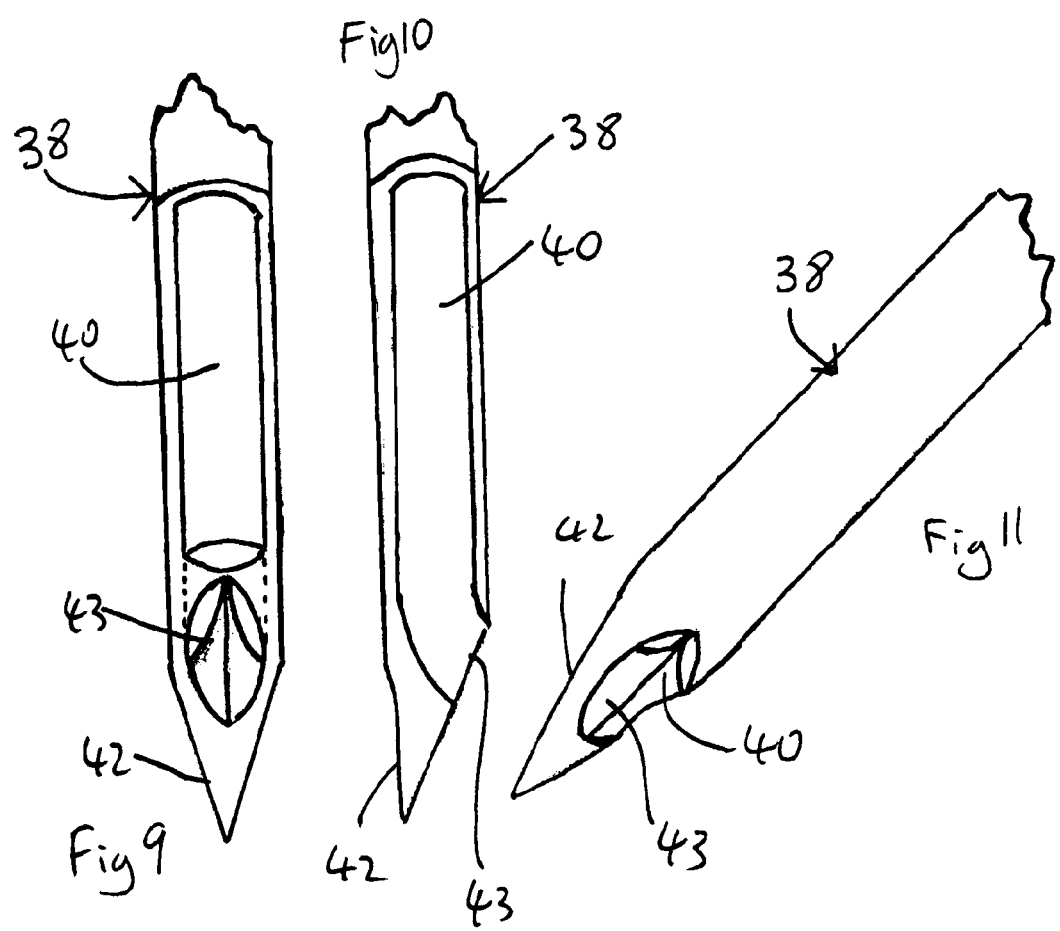

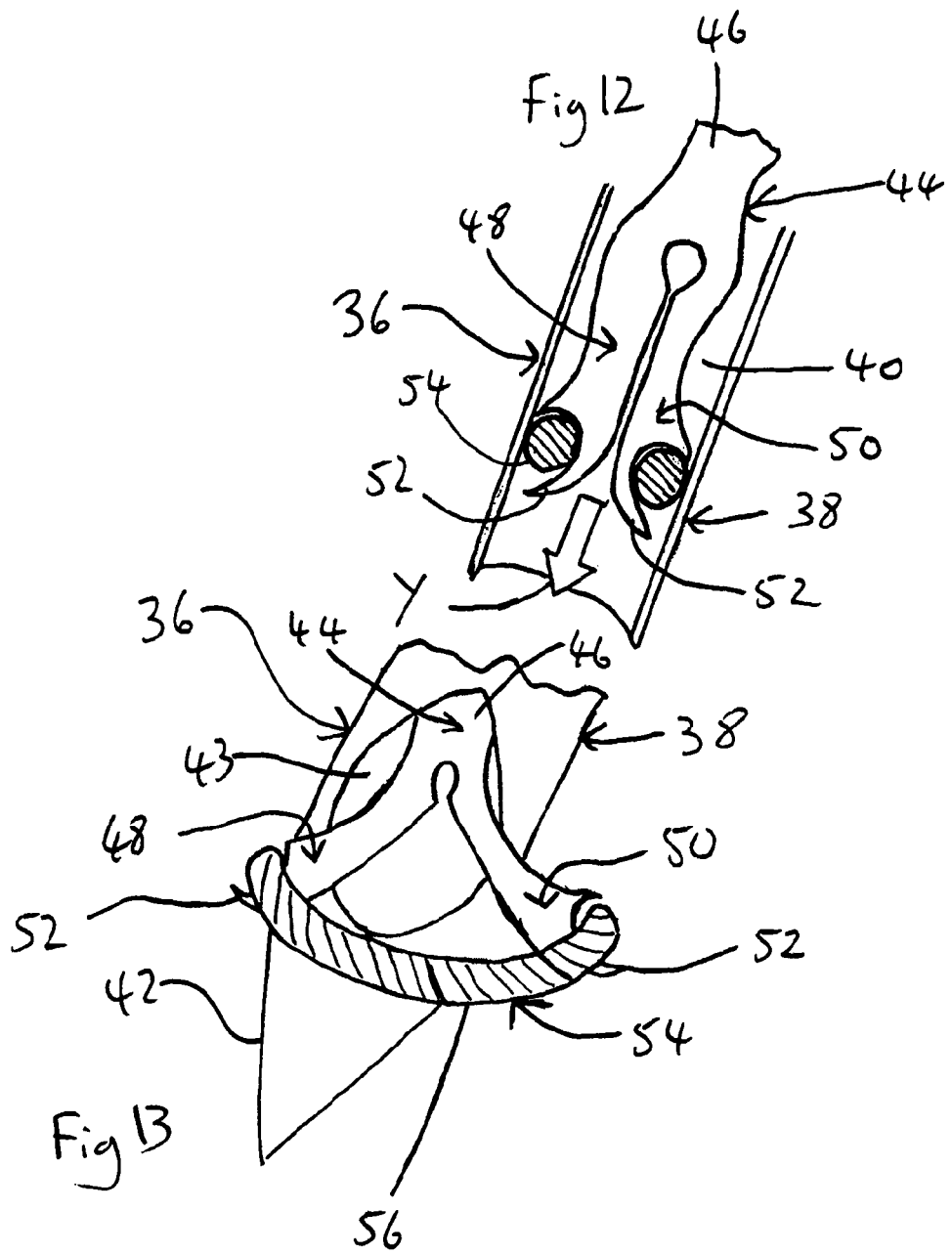

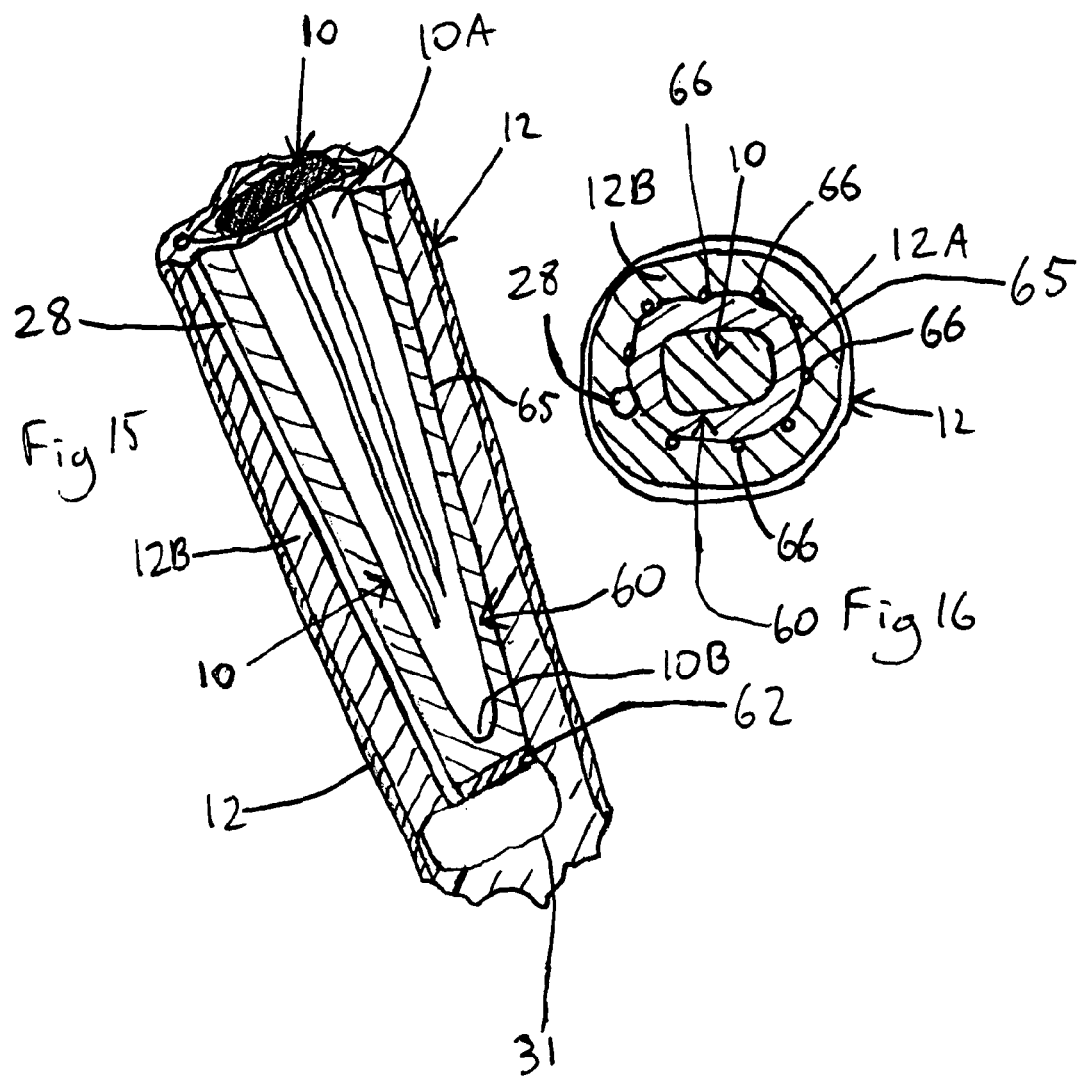

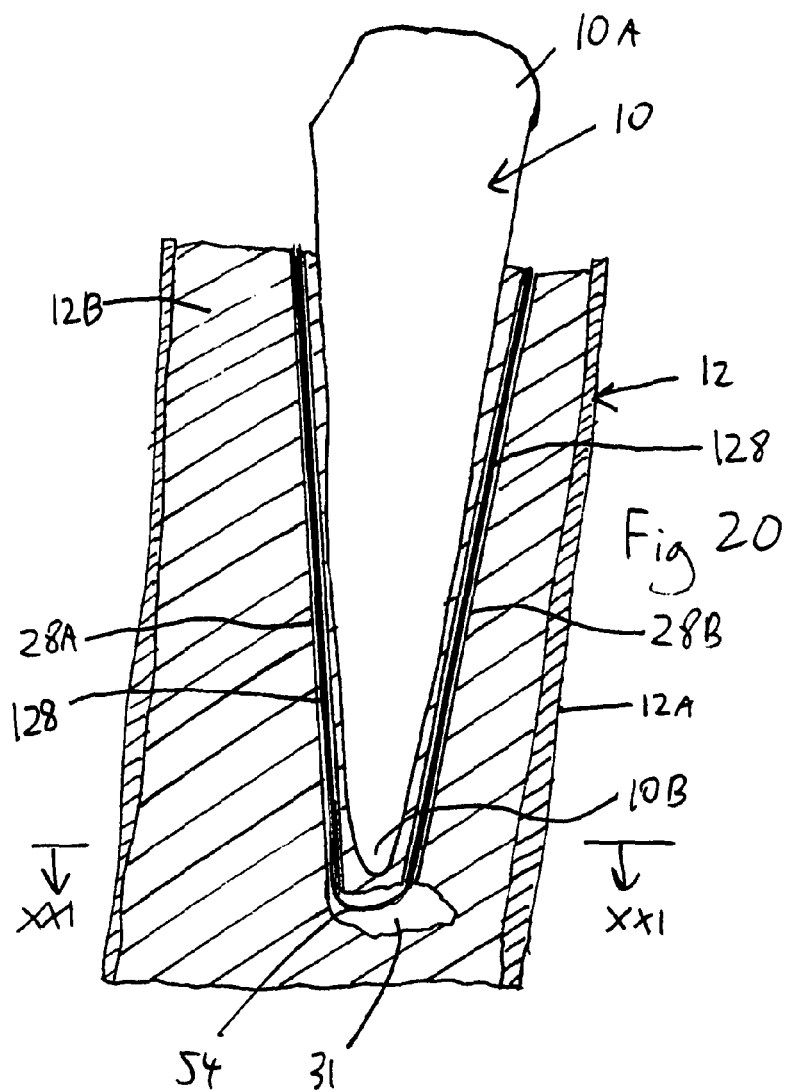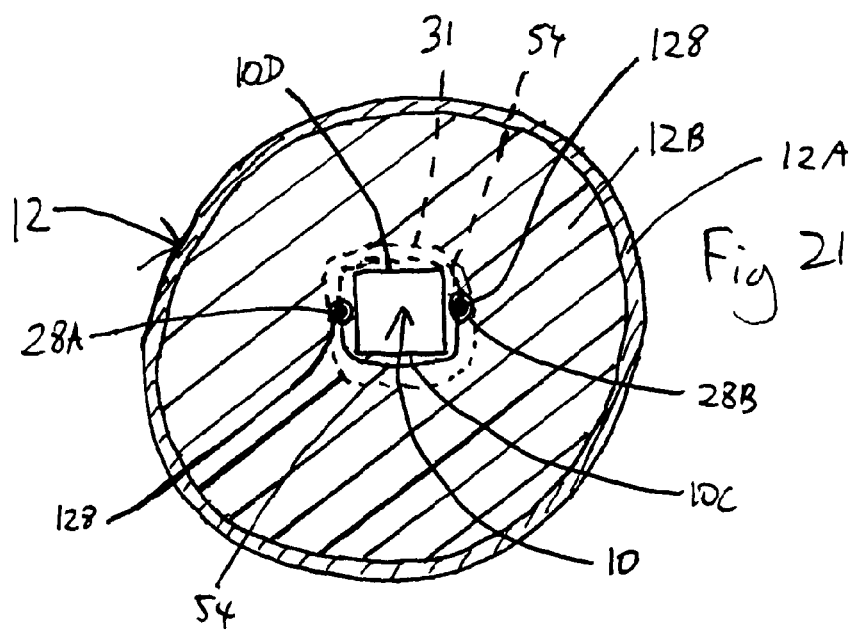

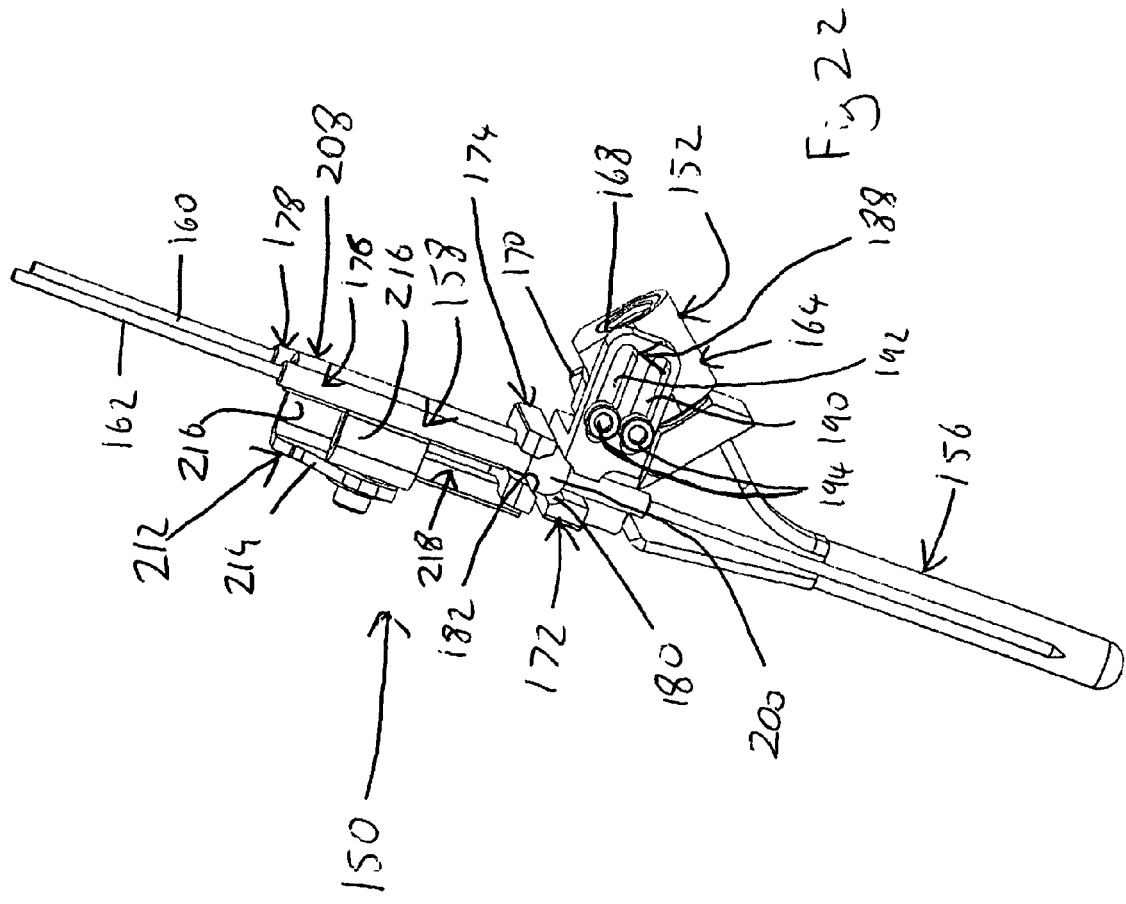

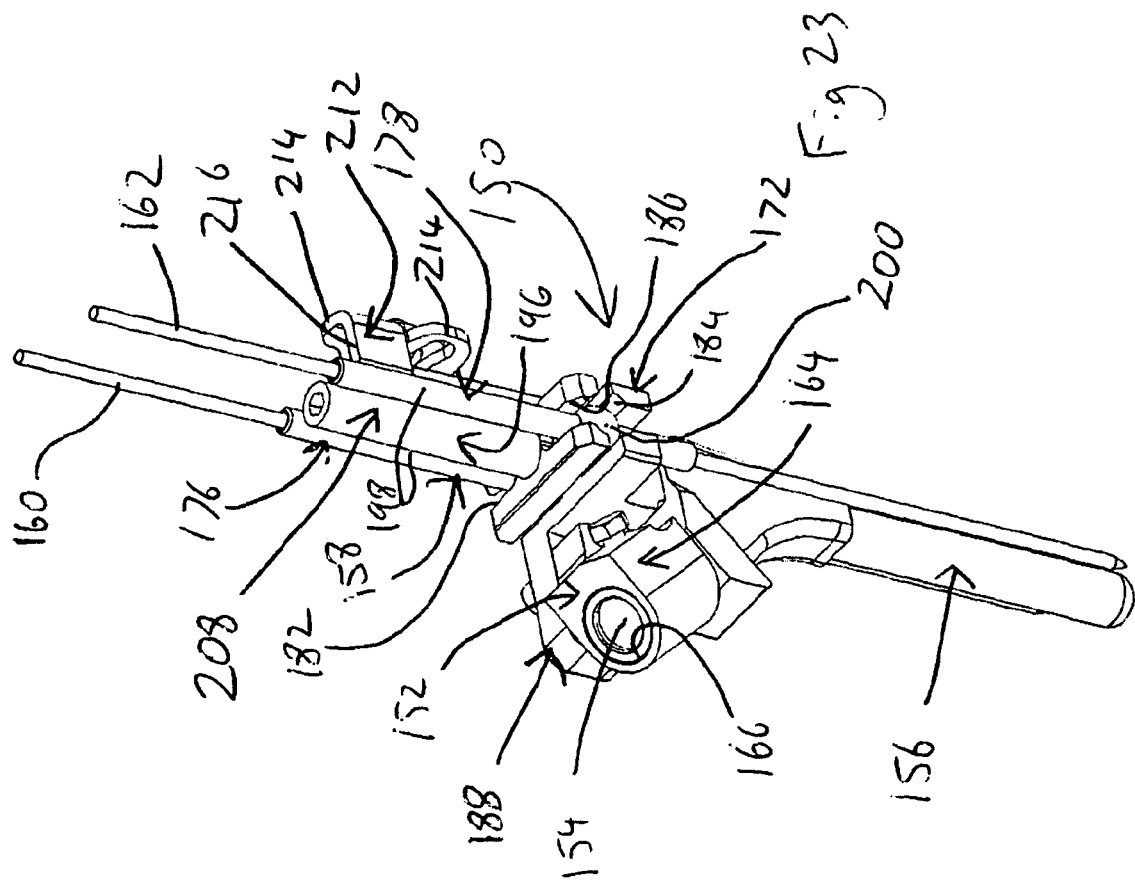

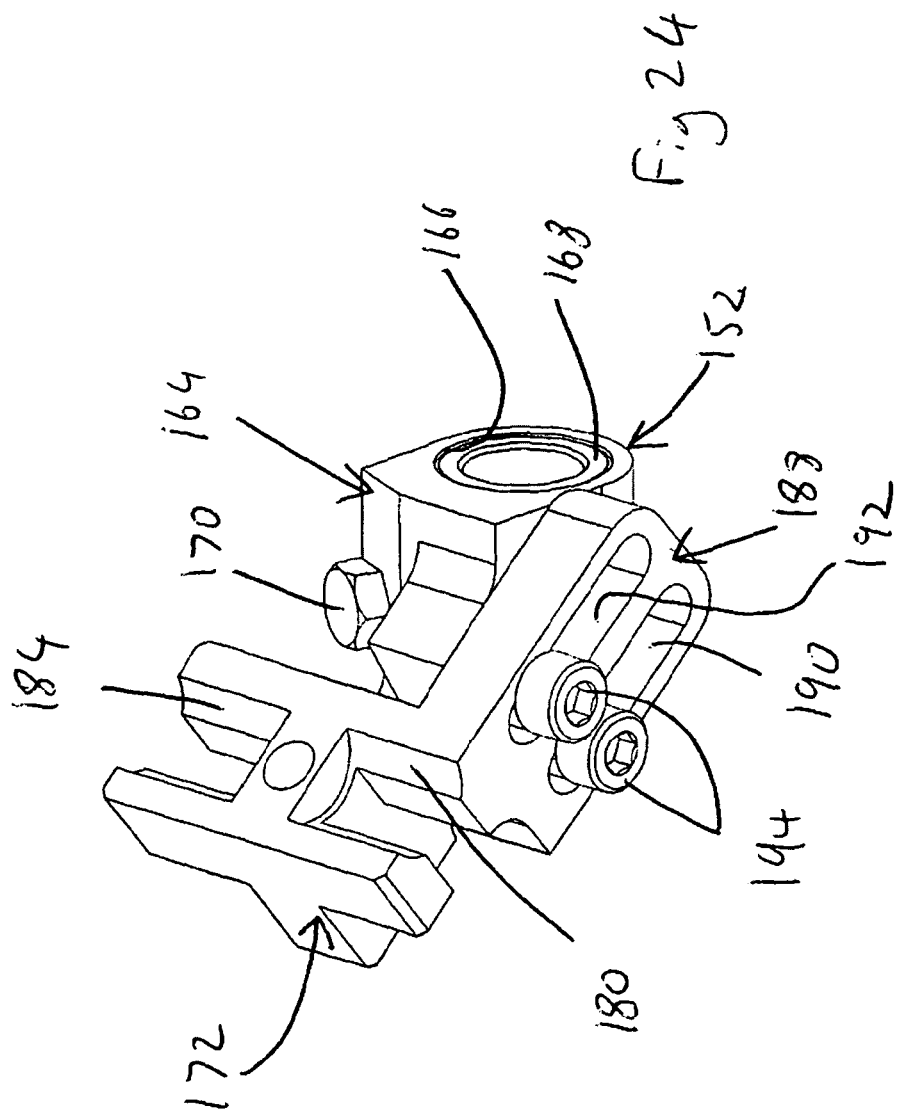

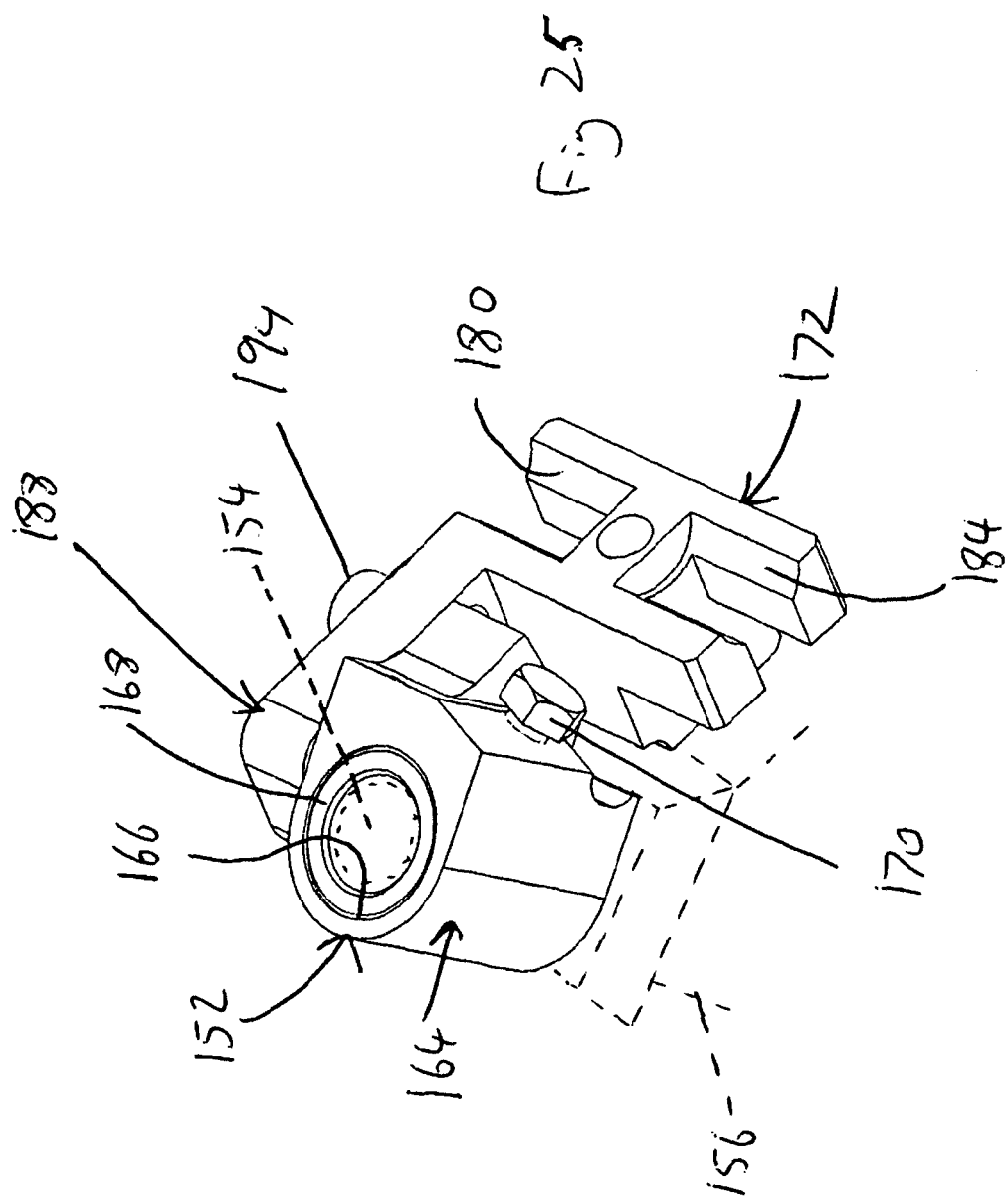

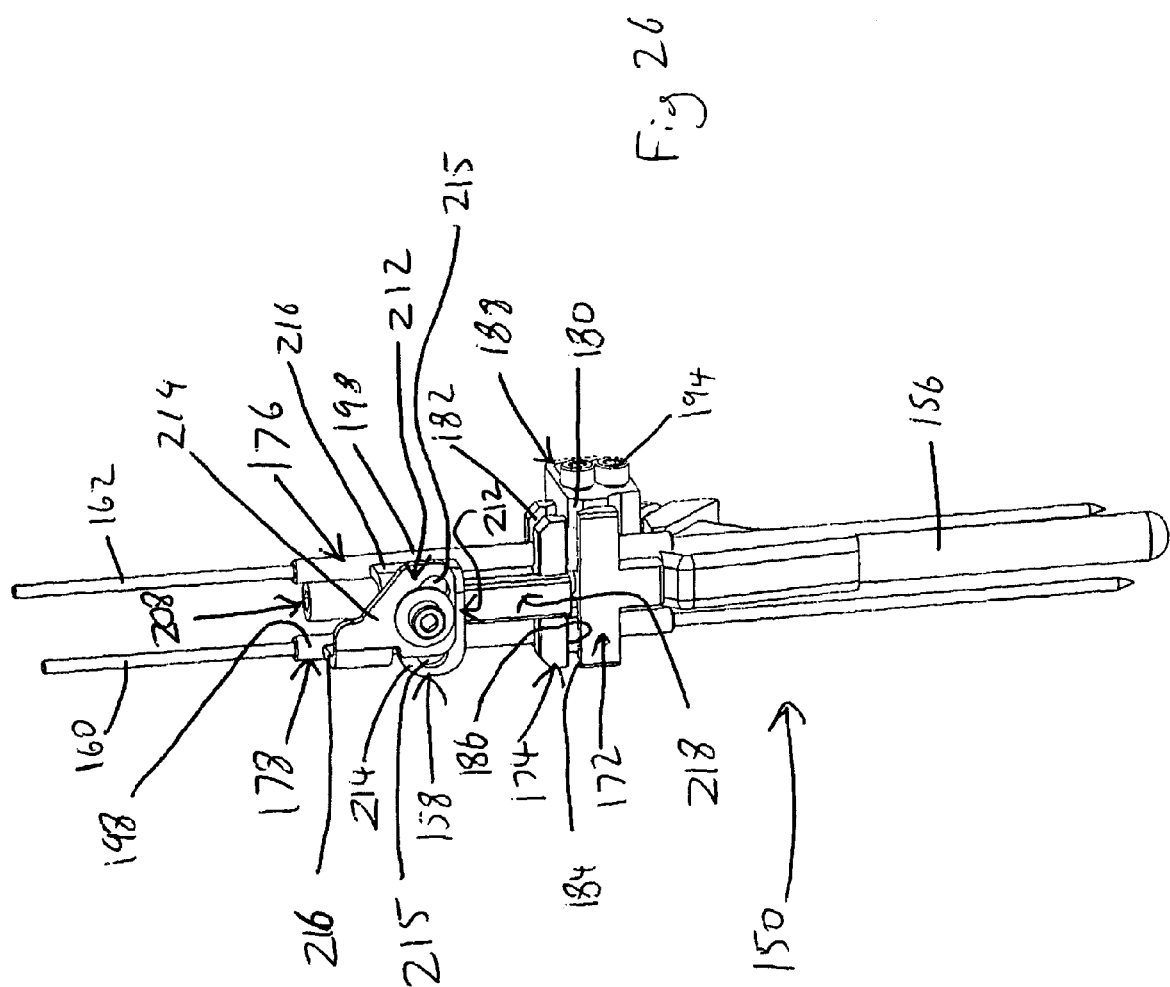

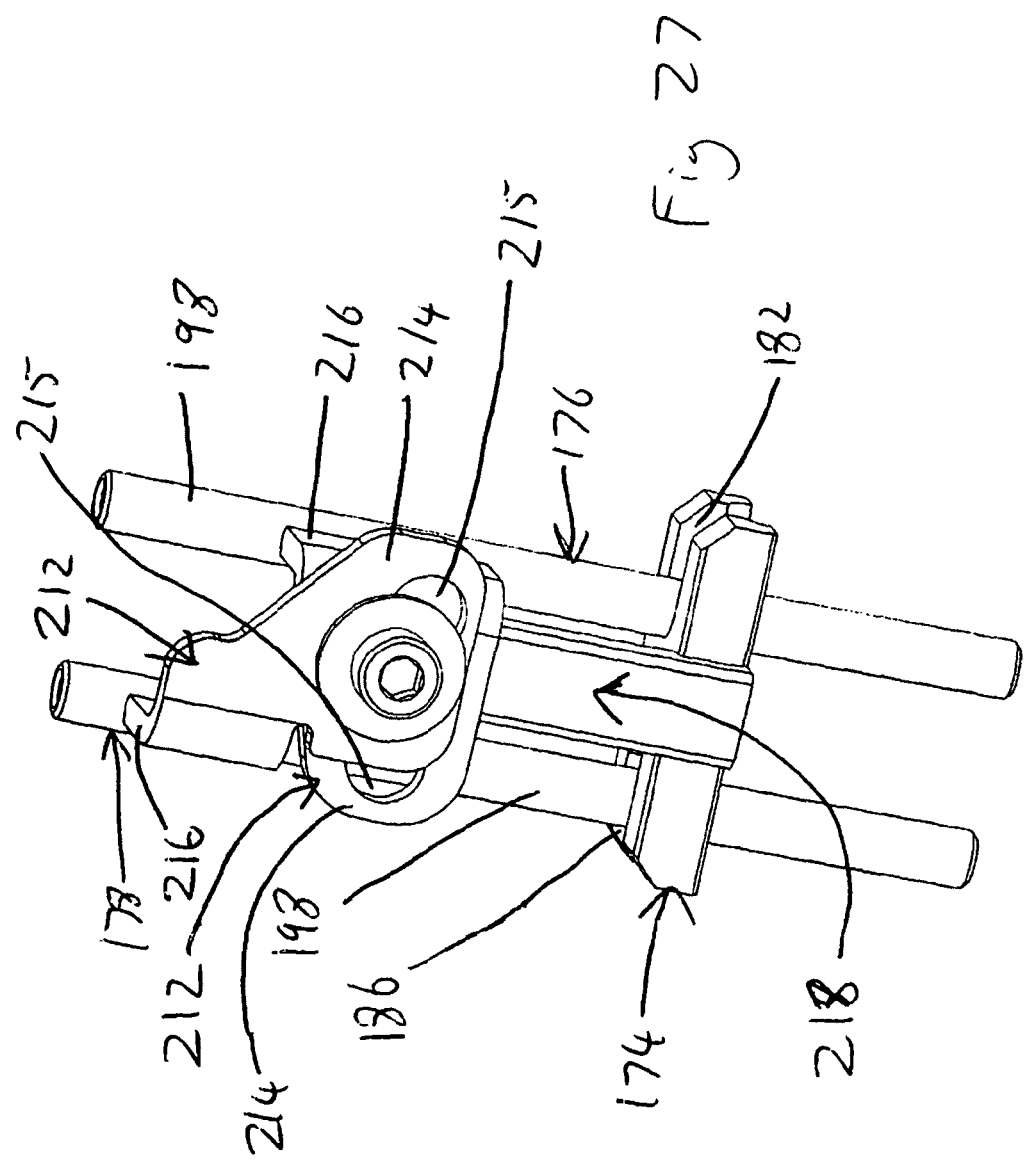

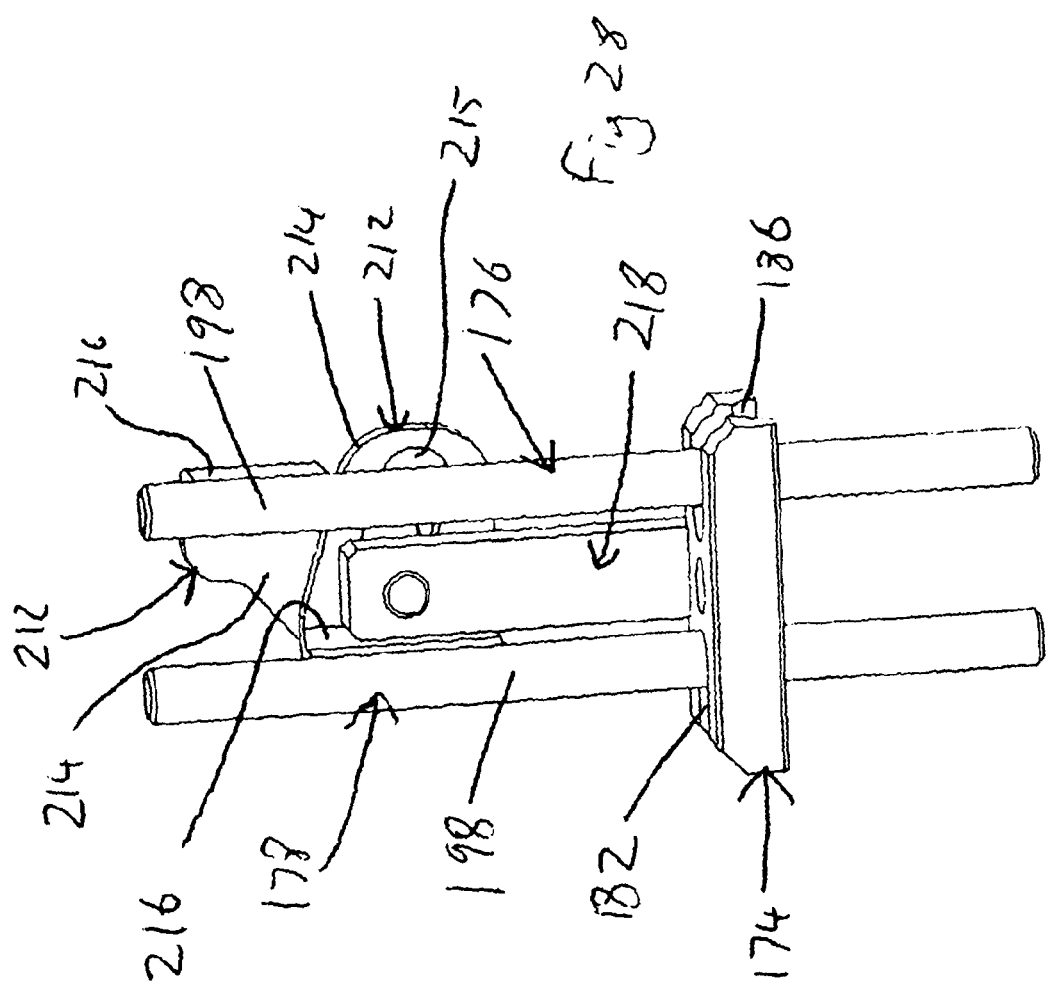

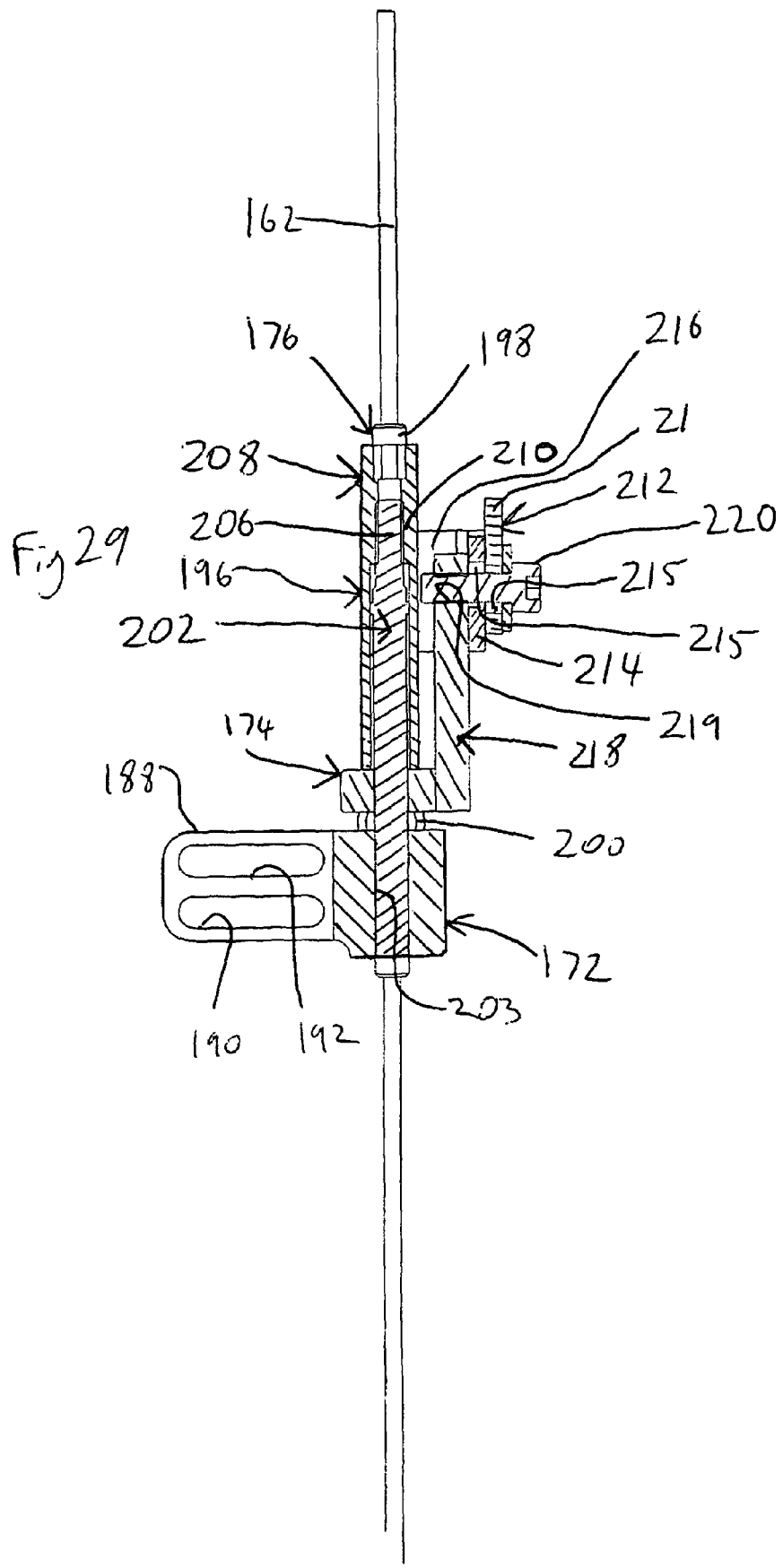

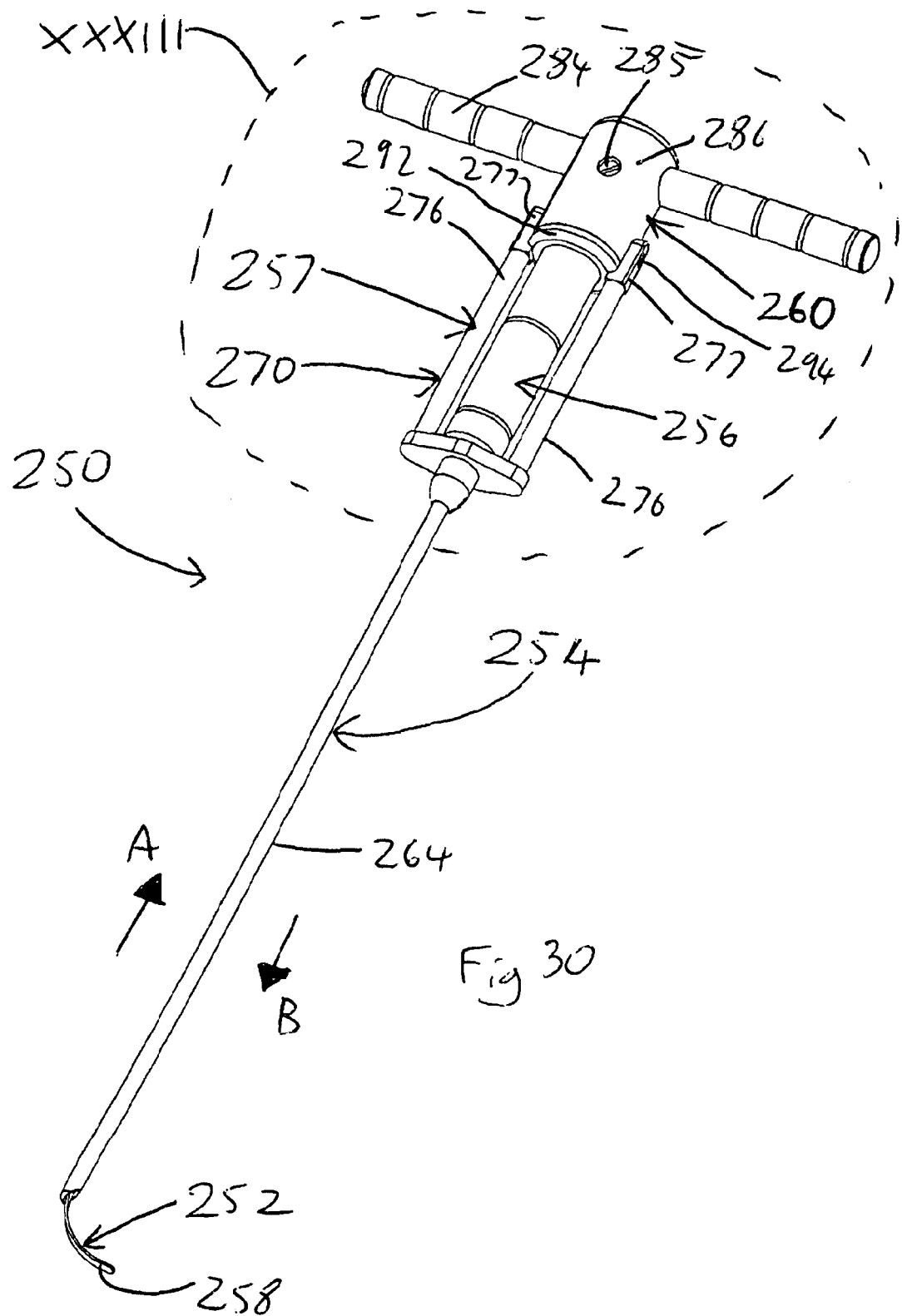

REMOVAL OF ARTICLES EMBEDDED IN SURROUNDING MATERIAL

PRIORITY

The present application is related to, claims the priority benefit of, and is a U.S. §371 national stage entry of International Patent Application Serial Number PCT/GB2010/001909, filed Oct. 14, 2010, which is related to, and claims the priority benefit of, U.S. provisional application Ser. No. 61/251,842, filed Oct. 15, 2009 and U.K. Patent Application Number GB0918006.8, filed Oct. 14, 2009, the disclosures of which are incorporated herein by reference.

FIELD OF THE INVENTION

This invention relates to methods of removing articles embedded in surrounding material. More particularly, but not exclusively, this invention relates to method of removing implants from bones, such as femoral implants

DESCRIPTION OF THE PRIOR ART

It is often necessary to remove bone implants that have previously been inserted, for example, where the implant has become loose, or the tissue surrounding the implant is infected. Such surgery requires all the cement surrounding the implant to be meticulously removed from the bone. Such removal is presently effected by the use of osteotomes or by the use of OSCAR cement removal equipment.

SUMMARY OF THE INVENTION

According to one aspect of this invention, there is provided a drill guide comprising a mounting arrangement for mounting the drill guide on an article embedded in surrounding material, first and second guide arrangements, a holding arrangement for holding the first and second guide arrangements, the holding arrangement being adjustable between a release condition in which the positions of the first and second guide arrangements are adjustable relative to the holding arrangement and a holding condition in which the first and second guide arrangements are held by the holding arrangement in a fixed position.

The guide arrangements may be pivotally adjustable relative to the holding arrangement.

Each of the first and second guide arrangements may comprise a guide member through which a drill can be inserted. The guide member may comprise a body defining an aperture therethrough. The body may be in the form of a tube. The drill may be received through the aperture. The aperture may be in the form of an elongate bore.

Each of the first and second guide arrangements may further include an adjustment member to allow adjustment of the position of the guide arrangement relative to the holding arrangement. The adjustment member may comprise a curved member, which may define a hole therethrough, so that the drill can extend through the hole. The curved member may have a spheroidal configuration, and may have an engagement face for engaging a part of the holding arrangement. The engagement face may be substantially planar.

Each guide arrangement may include a securing means to secure the guide arrangement to the holding arrangement. The securing means may comprise a securing portion that can be secured to the holding arrangement. The securing portion may define an aperture, which may be in the form of a slot. A fastening member may extend through the slot to secure the securing portion to the holding arrangement.

The securing means may comprise a connecting portion to connect the securing portion to the guide member.

The securing portion of one of the first and second guide arrangements may be configured to overlap the securing portion of the other of the first and second guide arrangements. Thus, in one embodiment, the fastening member may extend through the slots of the securing portions of each of the first and second guide arrangements.

The holding arrangements may comprise first and second holding members which are configured to engage the first and second guide arrangements therebetween. The first and second holding members may engage the adjustment member of each of the first and second guide arrangements. Tightening means may be provided to tighten the first and second holding members onto the adjustment members.

Each of the first and second holding members may comprise a first region to engage the adjustment member of the first guide arrangement, and a second region to engage the adjustment member of the second guide arrangement. In use, the adjustment members may be sandwiched between the first and second holding members.

Each of the first and second holding members may be generally H shaped.

The tightening means may comprise a first tightening member on the first holding member. The tightening member may extend through the second holding member. A second tightening member may be provided to co-operate with the first tightening member to urge the first and second holding members into the holding condition. The first and second tightening members may be threaded so that the first and second tightening members can be threaded onto each other.

A securing member may be provided on one of the first and second holding members. A fastening member may be co-operable with the securing member to secure the first and second guide arrangements thereto. The fastening member may extend through the securing portions of each of the first and second guide arrangements to co-operate with the securing member on the first or second holding member. The securing member may be provided on the second holding member and may extend there from. The securing member may be elongate.

The holding arrangement may comprise attaching means to attach the holding arrangement to the mounting arrangement. The attaching means may comprise an attaching member which extends transverse from the first or second holding member. In one embodiment, the attaching member extends transverse from the first holding member.

The attaching member may comprise a pair of slots through which the fastening members, such as bolts can extend to co-operate with corresponding apertures in the mounting arrangement. The provision of the slots allows the position of the holding arrangement to be adjusted on the mounting arrangement.

The mounting arrangement may comprise a mounting member defining a bore through which a projection on the embedded article can be received. The mounting arrangement may further include a fastening member which can be received in a threaded aperture defined in the mounting member. The threaded aperture may threadably receive the fastening member.

The mounting member may further define attaching apertures to which the fastening members on the attaching means can be threadably received.

The mounting arrangement may further include a shim member arranged in the bore in the mounting member between the mounting member and the projection on the mount. The shim member may define a slot through which the fastening member can be received to engage the projection on the mount.

The embedded article may comprise a bone implant, such as a hip replacement implant in a femur.

According to another aspect of this invention, there is provided a delivery device for delivering an elongate article, the delivery device comprising a delivery arrangement, and a support arrangement for supporting the delivery arrangement, wherein the delivery arrangement is pivotally mounted on the support arrangement and can move pivotally relative to the support arrangement to deliver the elongate article.

The delivery device may comprise first and second delivery arrangements, each of the first and second delivery arrangements being arranged to deliver respective first and second portions of the elongate article.

Each of the first and second delivery arrangements may be pivotally mounted on the support means.

The first and second delivery arrangements may be pivotally mounted on the support arrangement on opposite sides thereof.

The support arrangement may have a guide member to guide delivering of the elongate article. The guide member may comprise a curved element, which may provide a path for the elongate article.

The support arrangement may comprise directing means to direct the elongate article to a position where a portion of the elongate article is required. The directing means may comprise first and second elongate tubular members through which this elongate article can extend. The tubular members may extend from the support arrangement.

The support arrangement may include a holder to hold the directing means. The holder may define first and second bores at which the first and second tubular members can be mounted. Desirably, the first and second tubular members are held in the first and second bores. The guide member may be arranged to guide the elongate article into one of the first and second bores of the holder.

Each of the first and second delivery arrangements may comprise a delivery member, which may be pivotally attached to the support arrangement at a central region of the delivery member.

Each delivery member may have a distal end at which a gripping region may be provided. The elongate article may be gripped at the gripping region. Each of the first and second delivery arrangements may include a gripping element mountable on the respective delivery member at the gripping region. A threaded bolt member may be inserted through the gripping member and threadably received in the support member at the gripping region. Thus, the elongate article is gripped between the gripping member and the gripping region of the delivery member of each of the first and second delivery arrangements.

Each delivery member may have a proximal end at which a handle may be provided. The handle may comprise a ring through which a finger or thumb of the user can be inserted. The support arrangement may comprise a support member having a distal end at which the guide means may be provided. The support member may have a proximal end at which a handle may be provided. The handle may be in the form of a ring for receiving a finger or a thumb therethrough.

According to another aspect of this invention, there is provided surgical apparatus comprising a cavity forming arrangement, a movable housing for housing at least a portion of the cavity forming arrangement, and a rotatable sleeve through which the housing extends, wherein the housing and the sleeve comprise corresponding threaded formations in co-operation with each other, such that rotation of the sleeve causes movement of the housing.

The sleeve may comprise a movable barrel, which may be a rotatable barrel. The housing may be movable linearly relative to the sleeve when the sleeve is rotated.

The apparatus may further include an anti-rotation arrangement configured to restrict rotation of the housing relative to the cavity forming arrangement. Desirably, the anti-rotating arrangement is configured to restrict said rotation of the cavity forming arrangement to the extent that said rotation is substantially prevented.

The anti-rotating arrangement may be fixedly mounted on the cavity forming arrangement, or may be integral therewith.

The anti-rotating arrangement may comprise a first co-operating member, and the housing may comprise a second co-operating member. The first and second co-operating members may co-operate with each other to restrict rotation of the housing.

In one embodiment, the first and second co-operating members may comprise respective first and second elongate elements, which may engage one another. The first and second elongate elements may be telescopically receivable relative to each other, such that one of the first and second elongate elements telescopically receives the other of the first and second elongate elements. In one embodiment, the first elongate element may telescopically receive the second elongate element.

The first elongate elements may comprise elongate receiving elements. The second elongate elements may comprise elongate insertion elements.

The anti-rotating arrangement may comprise a pair of the first co-operating members, and the housing may comprise a pair of the second co-operating members. Desirably, the sleeve is arranged between the pair of the first co-operating members, and between the pair of second co-operating members.

The anti-rotating arrangement may comprise a bush through which the sleeve can extend. The sleeve may have a radially outwardly extending flange to engage a radially inwardly extending portion of the bush, thereby holding the sleeve within the anti-rotating arrangement.

The, or each, first co-operating member may be secured to the bush. The anti-rotating arrangement may further include a cover member, and the bush may be received in the cover member. The cover member may be secured to the cavity forming arrangement, for example by a screw extending through the cover to engage the cavity forming arrangement.

A handle may extend through the cover member and may be secured thereto, for example by a screw.

The cavity forming arrangement may comprise a torque transmission member having a proximal end and a distal end. The torque transmission member may comprise shaft, and may be secured to the anti-rotating arrangement, desirably at the proximal end. A cavity forming element may be provided at the distal end of the shaft. The cavity forming element may comprise a cutting ribbon.

The housing may comprise an elongate tubular portion through which the torque transmission member extends.

The cavity forming element may comprise a curved member which may be flexible. The movement of the housing may be such that the housing extends over the cavity forming element, and when the sleeve is rotated in the extending direction, the cavity forming element may extend from the housing and return to its curved configuration.

According to another aspect of this invention, there is provided a guide for an elongate cutter, the guide comprising a mounting apparatus for mounting the guide on an article, a guide assembly, and a support arrangement for supporting the guide assembly.

The guide assembly comprises a carrier and at least one guide member. The carrier may be slidably connected to the support arrangement. The guide member may define a gap for the cutting member. A fastener, such as a bolt may be provided to fasten the carrier to the support arrangement.

The guide member may comprise an elongate element on the carrier. The elongate element may define the aforesaid gap. The gap may be defined between the guide member and the carrier.

The elongate element may have opposite ends. Each opposite end may be attached to the carrier, whereby the gap is defined between the elongate element and the carrier.

The guide assembly may comprise a pair of the aforesaid guide member. Each guide member may be attached to the carrier at a respective opposite side of the carrier.

The carrier may define an adjustment formation to co-operate with a fastener, and allow the position of the carrier on the support member to be adjusted. The adjustment formation may be a slot defined in the carrier. The fastener may extend through the slot to fasten the carrier to the support member.

The guide may further include locating assembly for locating the guide assembly relative to the article. The locating assembly may be mounted on the support arrangement and may extend therefrom to engage the article. The locating assembly may be configured to engage the article on opposite sides thereof.

The locating assembly may comprise a clamping arrangement and a locating member, wherein the clamping arrangement clamps the locating member. Desirably, the clamping arrangement clamps the locating member to the support member.

The locating assembly may comprise a pair of locating members, each being provided on a respective opposite side of the support arrangement. The, or each, locating member may be elongate.

The clamping arrangement may extend through the support arrangement. The clamping arrangement may comprise a pair of clamping members, each being configured to clamp a respective one of the locating members. Each clamping member may comprise a clamping portion to engage the respective locating member.

Each clamping member may further include a projecting portion to extend through an aperture in the support arrangement. A fastener, such as a bolt may extend through the clamping members to fasten the clamping members to each other.

The mounting apparatus may comprise attaching means to attach the support arrangement to the mounting apparatus. The attaching means may comprise an attaching member which extends transverse from the support arrangement The support member may define a pair of apertures through which the fastening members, such as bolts can extend to co-operate with corresponding apertures in the attaching means.

The mounting apparatus may be provided on the support arrangement and may comprise a mounting member defining a bore through which a projection on the embedded article can be received. The mounting apparatus may further include a fastening member which can be received in a threaded aperture defined in the mounting member. The threaded aperture may threadably receive the fastening member.

The mounting member may further define attaching apertures to which the fastening members extending through the support arrangement can be threadably received.

The mounting apparatus may further include a shim member arranged in the bore in the mounting member between the mounting member and the projection on the mount. The shim member may define a slot through which the fastening member can be received to engage the projection on the article.

The support arrangement may comprise a support member to which other components can be connected. The support member may define an aperture, through which the, or each, locating assembly can extend.

According to another aspect of this invention, there is provided a method of removing an article embedded in surrounding material, the method comprising forming an access tunnel through the material adjacent the embedded article, said access tunnel extending from a proximal end of the embedded article to a region beyond a distal end of the embedded article, forming a cavity in the material at the region beyond the distal end of the embedded article, delivering at least a portion of a cutting member to the distal end of the embedded article, driving the cutting member to cut the material adjacent the embedded article to allow the embedded article to be removed from the material.

The cutting member may comprise a flexible elongate member. The step of delivering at least a portion of a cutting member may comprise delivering a portion of the flexible elongate member into the cavity.

The portion of the flexible elongate member so delivered may be a loop of the flexible elongate member.

The step of driving the cutting member may include driving the flexible elongate member along its length. The step of driving the cutting member may include withdrawing the flexible elongate member through the, or each, access tunnel.

The step of withdrawing the flexible elongate member may comprise withdrawing the flexible elongate member while the flexible elongate member is being driven.

The step of withdrawing the flexible elongate member through the access tunnel may effect cutting of the material along the length of the embedded article. At least a portion of the wall of the access tunnel may be a region of the embedded article.

In the embodiments of the invention described herein, the driving of the flexible elongate member while withdrawing the flexible elongate member through the access tunnel may cause the flexible elongate member to cut the material as it is being withdrawn.

The embedded article may comprise an implant, which may be implanted into a bone, such as a femur. The material surrounding the embedded article may comprise bone, such as cancellous bone.

In one embodiment, the step of forming the access tunnel may comprise forming an incision between the embedded article and the surrounding material. The step of forming the incision may comprise forming a recess in the material adjacent the embedded article.

The step of forming the incision may include inserting an incising device between the embedded article and the surrounding material. Desirably, the incising device is so inserted in contact with the embedded article. The incising device may comprise an osteotome.

The step of forming the incision may include moving the incising device along the embedded article, in contact with the embedded article. The step of forming the incision may include removing material from a region of the embedded article.

The step of forming the incision may include removing material from the embedded article over a distance of up to about 3 cm. Desirably, the step of forming the incision includes removing material from the embedded article over a distance of up to about 2 cm. In one embodiment, the step of forming the incision may include removing material from the embedded article over a distance of between 1 and 2 cm.

The step of forming the access tunnel may include inserting a guide member into the recess formed by the incising device. The guide member may comprise a drill guide. Alternatively, the step of forming the access tunnel may comprise mounting a drill guide on the embedded article.

The step of forming the access tunnel may include drilling the access tunnel.

The access tunnel may have a diameter of between 2 mm and 4 mm. Desirably, the access tunnel may have a diameter of substantially 3 mm.

The step of forming the cavity may comprise disposing a cavity forming apparatus in the access tunnel. The cavity forming apparatus may comprise a rotatable cutting apparatus.

The cutting apparatus may comprise a torque transmission member, which may comprise an elongate shaft having a longitudinal axis. The cutting apparatus may further include one, or a plurality of cavity forming elements at one end region of the torque transmission member. The, or each, cavity forming element may comprise a cutting filament or ribbon.

The torque transmission member may have a proximal end region and a distal end region, and the, or each, cavity forming element may be provided at the distal end region of the torque transmission member.

The cavity forming elements may comprise a plurality of elongate strands. The cavity forming elements may extend generally radially outwardly relative to the torque transmission member. The cavity forming elements may extend radially, tangentially, or between radially and tangentially relative to the torque transmission member.

The step of forming the cavity may comprise inserting the cavity forming apparatus into the access tunnel until the, or each, cavity forming element reaches the region beyond the distal end of the embedded article.

The step of forming the cavity may include rotating the, or each, cavity forming element to cut the material at the region beyond the distal end of the embedded article, thereby removing said material from the aforesaid region beyond the distal end of the embedded article.

The step of rotating the, or each, cavity forming element may comprise rotating the torque transmission member about its longitudinal axis.

The step of delivering at least a portion of the cutting member may comprise providing a delivery arrangement in the access tunnel with which the portion of the cutting member can be delivered.

The delivery arrangement may comprise a delivery housing through which the cutting member can pass. The delivery housing may comprise a delivery tube.

The delivery housing may define an elongate channel therethrough. The flexible elongate member may pass through the channel. The channel may have an entrance opening at a proximal end of the delivery housing. The entrance opening may be an axial opening.

The delivery housing may have a peripheral wall, which may be circumferential. The channel may have a delivery opening at a distal end of the delivery housing. The delivery opening may be an opening in the peripheral wall of the delivery housing. The distal end of the delivery housing may be pointed.

The step of the delivering at least a portion of the cutting member into the cavity may comprise inserting the flexible elongate member through the channel and out of the delivery opening.

The delivery arrangement may include a delivery member, which may have at least two co-operating members to co-operate with the cutting member, to provide an engagement portion of the cutting member, whereby the engagement portion can be manipulated by the co-operating members around the embedded article.

The delivery member may comprise an elongate portion to allow the delivery member to be inserted through the delivery housing. The co-operating members may be provided at one end of the elongate portion.

The co-operating members may be movable between retracted and expanded positions. The co-operating members may be urged from the retracted position to the expanded position.

In one embodiment, the co-operating members may be formed of a resilient material which urges the co-operating members from the retracted to the expanded positions.

Each co-operating member may include a holding element to hold the cutting member. Where the cutting member comprises a flexible elongate member, a loop of the flexible elongate member desirably extends between the holding elements of each co-operating member. Each holding element may comprise a hook element to hook around the flexible elongate member.

The co-operating members may comprise a forked arrangement, wherein when the co-operating members are in the expanded position, the co-operating members fork away from each other, and when the co-operating members are in the retracted position, the cooperating formations lie alongside each other. The delivery housing may hold the co-operating members in the retracted position.

The step of delivering the cutting member may include delivering the portion of the cutting member into the cavity. The step of delivering the cutting member may include inserting the delivery member into the access tunnel until the second aperture is at the cavity The step of delivering the cutting member may include arranging said portion of the flexible elongate member to extend between the holding elements.

The step of delivering the cutting member may further include pushing the delivery member so that the co-operating members are moved out of the second aperture into the cavity, whereby the co-operating members move to the expanded position.

The step of delivering the cutting member may include arranging the loop of the flexible elongate member around the distal end of the embedded article.

The flexible elongate member may comprise a cutting portion and a delivery portion by which the cutting member is delivered to the embedded article. The loop may be generally smooth. The cutting portion may include a plurality of cutting formations arranged along the length of the cutting portion. The loop may be between 15 and 25 cm in length. Desirably, the loop is substantially 20 cm in length.

The cutting member may be part of a cutting apparatus, which may include a guide sheath through which in the flexible elongate member can extend. The guide sheath may have a proximal end region adjacent a driving device, and a distal end region out of which the flexible elongate member can extend. The guide sheath may comprise a cable housing. The flexible elongate member may be driven by the driving device.

The step of driving the cutting member may include providing the guide sheath in the access tunnel so that the distal end region of the guide sheath is adjacent the distal end of the embedded article. The flexible elongate member may then be driven around the embedded article thereby cutting material around the embedded article.

The step of withdrawing the flexible elongate member through the access tunnel may comprise withdrawing the guide sheath through the access tunnel in the direction from the distal end to the proximal end of thereof, thereby causing the flexible elongate member to be dragged along the embedded article from the distal end to the proximal end. This feature has the advantage in the embodiment described herein that the material is removed from the embedded article during said dragging of the flexible elongate member.

In a second embodiment, a second access tunnel may be formed in the material adjacent the embedded article. The second access tunnel may be spaced from the first mentioned access tunnel.

The second access tunnel may extend from the proximal end of the embedded article to the cavity beyond the distal end of the embedded article. The second access tunnel may be formed before or after the cavity is formed.

In the second embodiment, the first mentioned access tunnel and the second access tunnel may be formed opposite each other, with the embedded article therebetween.

In the second embodiment, the method may comprise inserting a first portion of the cutting member into the cavity via one of the access tunnels, and connecting said first portion to a second portion of the cutting member.

At least one of the first and second portions of the cutting member may have a connecting element thereon to connect the first and second portions to each other.

After the first and second portions of the cutting member have been connected to each other, the method may include cutting across a first region of the embedded article by driving the cutting member through the first mentioned access tunnel and through the second access tunnel, and pulling the cutting member through the material.

After the step of cutting across a first portion of the embedded article, the method may include inserting the first portion of the cutting member into the cavity via one of the access tunnels, and connecting said first portion to a second portion of the cutting member.

After the first and second portions of the cutting member have been connected to each other, the method may include cutting across a second region of the embedded article by driving the cutting member through the first mentioned access tunnel and through the second access tunnel, and pulling the cutting member through the material. The first region of the embedded article may be opposite the second region thereof.

The connecting of the first and second portions of the cutting member to each other may be effected by inserting the second portion of the cutting member into the cavity via the other of the access tunnels. The second portion may engage the first portion of the cutting member in the cavity and thereby connect the first and second portions to each other. The first and second portions of the cutting member may be first and second opposite end portions of the cutting member.

In a third embodiment, a plurality of guide members may be arranged around the embedded article. Each of the guide members may be elongate, and may be longer than the embedded article. Each guide member may comprise a wire. Suitably, each wire may be a K wire.

The third embodiment is suitable where the embedded article comprises a combination of an implant and cement surrounding the implant, wherein the cement secures the implant within the material, for example bone. In such cases, it is particularly desirable to remove the embedded article as a whole, i.e. to remove the implant and the cement.

The third embodiment is also suitable where the embedded article has a stepped configuration, wherein a step is provided between the distal and the proximal ends of the embedded article, such that the embedded article is wider at the proximal end region than the distal end region. The absence of the guide members may cause the cutting member to snag at the step.

The step of arranging the guide members around the embedded article may be effected before cutting the material with the cutting member. A plurality of elongate bores are formed around the embedded article. Each bore may extend from the proximal end region of the embedded article at least to the distal end region thereof. Each bore may extend beyond the distal end region of the embedded article.

The elongate bores may be formed at the junction between the embedded article and the material. The elongate bores may be formed by drilling, and each bore may be substantially 2 mm in diameter.

The elongate bores may be spaced one after the other around the embedded article. The elongate bores may extend from a region adjacent the proximal end of the embedded article to the cavity.

A respective guide member is arranged in each of the bores. When so arranged, the guide members may provide an enclosing cage around the embedded article.

The step of forming the access hole in the material may occur before the formation of the bores. The step of forming the cavity may occur before the formation of the bores. Each bore may extend to the cavity and may be in communication therewith.

Each guide member may be arranged in the respective bore, such that the distal end region of each guide member extends into the cavity. The distal end region of each guide member may be curved so that, when each guide member is received in the respective bore, the distal end regions of the guide members converge inwardly toward the distal end of the embedded article.

The step of delivering the portion of the cutting member may comprise delivering the flexible elongate member such that the loop thereof is arranged around the converging distal end regions of the guide members.

The step of driving the cutting member may comprise a driving the cutting member around the guide members, thereby removing material from the cement surrounding the implant.

The step of withdrawing the flexible elongate member through the access tunnel may include moving the flexible elongate member through the access tunnel in the direction from the distal end to the proximal end of thereof, thereby causing the flexible elongate member to be dragged along the guide members from the distal ends to the proximal ends of the guide members. This feature had the advantage in the embodiment described herein that the material in contact with the cement surrounding the implant is removed during said movement of the elongate member along the guide members.

According to another aspect of this invention, there is provided material removal of apparatus comprising an elongate torque transmission member, a driver to rotate the torque transmission member, and a plurality of outwardly extending material removal members carried by the torque transmission member.

The torque transmission member may comprise a shaft, and the shaft may be connected to the driver. The torque transmission member may have a longitudinal axis, and the driver may rotate the torque transmission member about the longitudinal axis thereof. The torque transmission member may have a distal end and a proximal end.

The proximal end of the torque transmission member may be connected to the driver. The material removal members may be elongate. The material removal members may be provided at the distal end of the torque transmission member. The material removal members may be in the form of elongate elements, for example filaments, such as wires, spines or bristles.

The material removal apparatus may constitute the cavity forming apparatus described above.

According to another aspect of this invention, there is provided a delivery arrangement for delivering at least an engagement portion of a cutting member, the delivery arrangement comprising a delivery housing through which the cutting member can pass, and a delivery member receivable in the delivery housing, the delivery member comprising at least two co-operating members to co-operate with the cutting member to provide the engagement portion of the cutting member, whereby the engagement portion can be manipulated by the co-operating members.

The delivery housing may comprise a delivery tube.

The delivery housing may define an elongate channel therethrough. The cutting member may pass through the channel to deliver the cutting member.

The channel may have a first opening at a proximal end of the delivery housing. The first opening may be an axial opening.

The delivery housing may have a peripheral wall, which may be circumferential. The channel may have a second opening at a distal end of the delivery housing.

The second opening may be an opening in the peripheral wall of the delivery housing. The distal end of the delivery housing may be pointed to facilitate insertion of the delivery housing into a guide hole.

The delivery member may comprise an elongate portion to allow the delivery member to be inserted through the delivery housing. The co-operating members may be provided at one end of the elongate portion.

The co-operating members may be movable between retracted and expanded positions. The co-operating members may be urged from the retracted position to the expanded position.

In one embodiment, the co-operating members may be formed of a resilient material which urges the co-operating members from the retracted to the expanded positions.

Each co-operating member may include a holding element to hold the cutting member. Where the cutting member comprises a flexible elongate member, a loop of the flexible elongate member desirably extends between the holding elements of each co-operating member. Each holding element may comprise a hook element to hook around the flexible elongate member.

The co-operating members may comprise a forked arrangement, wherein when the co-operating members are in the expanded position, the co-operating members may fork away from each other, and when the co-operating members are in the retracted position, the cooperating formations may lie alongside each other. The delivery housing may hold the co-operating members in the retracted position.

BRIEF DESCRIPTION OF THE DRAWINGS

Embodiments of the invention will now be described by way of example only, with reference to the accompanying drawings, in which:

FIG. 9 is a part sectional front view of a distal end of part of a delivery arrangement;

FIG. 10 is a part sectional side view of the distal end of the part of the delivery arrangement shown in FIG. 9;

FIG. 11 is a side perspective view of the distal end of the part of the delivery arrangement shown in FIG. 9;

FIG. 12 shows a portion of a delivery member delivering a cutting member through the part shown in FIGS. 9, 10 and 11;

FIG. 13 shows the portion of the delivery member shown in FIG. 12 delivering the cutting member;

FIG. 15 is a sectional side view of part of an implant and of a bone showing a further embodiment;

FIG. 16 is a top view of the part shown in the FIG. 15 after the insertion of a plurality of enclosing wires;

FIG. 20 is a sectional side view of the surgical implant in a femur two access tunnels for the cutting member;

FIG. 21 is a view along the lines XXI-XXI in FIG. 20;

FIG. 22 is a side view of an embodiment of a drill guide;

FIG. 23 is a rear perspective view of the drill guide shown in FIG. 22;

FIG. 24 is a view from one side of a first holding member for use in the drill guide shown in FIG. 22;

FIG. 25 is a view from the opposite side of the first holding member

FIG. 26 is a front view of the drill guide shown in FIG. 22;

FIG. 27 is a front view of first and second guide arrangements;

FIG. 28 shows a rear view of the first and second guide arrangements;

FIG. 29 is a sectional side view of the first and second guide arrangements;

FIG. 30 is a perspective view of a surgical apparatus for forming a cavity;

DESCRIPTION OF PREFERRED EMBODIMENTS

Figure 1:
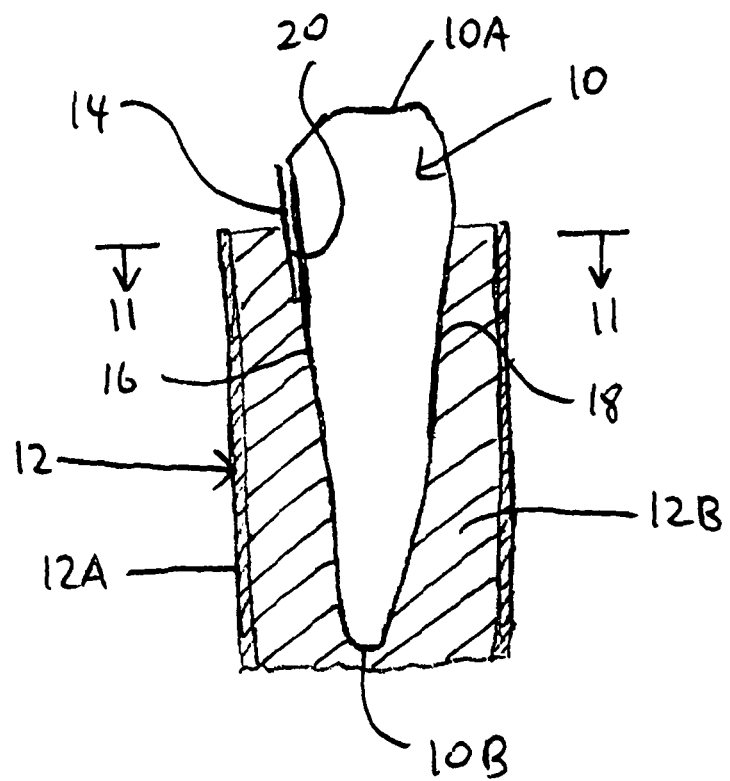
FIG. 1 is a sectional side view of a surgical implant in a femur showing a recess being cut in the bone adjacent the implant.
Figure 2:
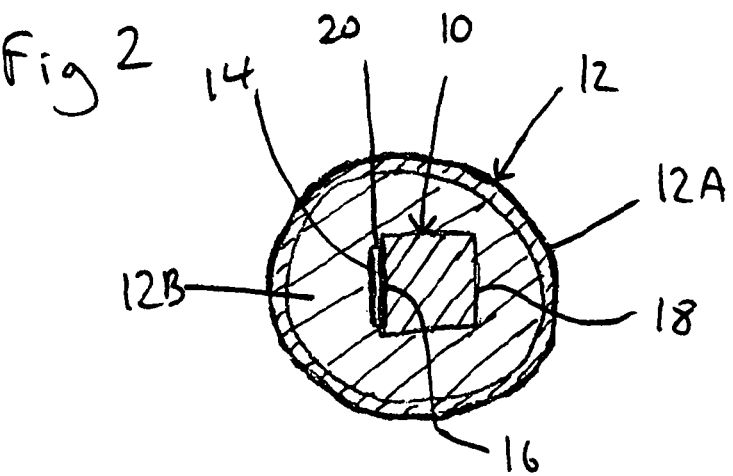
FIG. 2 is a view along the lines II-II in FIG. 1.

Referring to the drawings, FIGS. 1 to 14 show an embodiment for removing an implant from the femur of a patient, the implant having a previously been implanted during, for example, hip replacement surgery.

In the drawings, the implant is generally designated with the numeral 10, and the femur is generally designated with the numeral 12. The femur 12 comprises a cortex 12A surrounding cancellous bone tissue 12B.

The implant 10 is implanted in the cancellous bone tissue 12B, and has a proximal end 10A and a distal end 10B. After the preliminary stages of dislocating the joint and removing soft-tissue from the proximal regions of the femur 12, an osteotome 14 is provided (see FIGS. 1 and 2).

The osteotome is arranged in engagement with the anterior face 16, or with the posterior face 18, of the implant 10. In the embodiment shown, the osteotome is arranged in engagement with the anterior face 16 at the implant/bone interface.

The osteotome 14 is used to cut bone away from the implant 10 to a distance of approximately 1 to 2 cm inwards of the cancellous bone tissue 12B, longitudinally of the femur 12, and of the implant 10, to form a recess 20 extending adjacent the implant 10.

Figure 3:
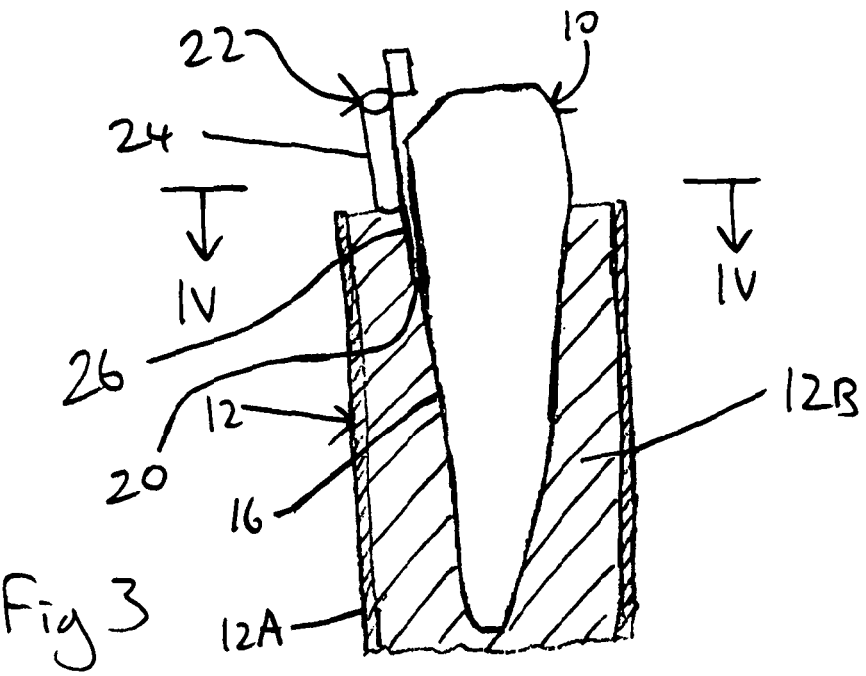
FIG. 3 is a view similar to FIG. 1 showing the insertion of a drill guide in the recess.
Figure 4:
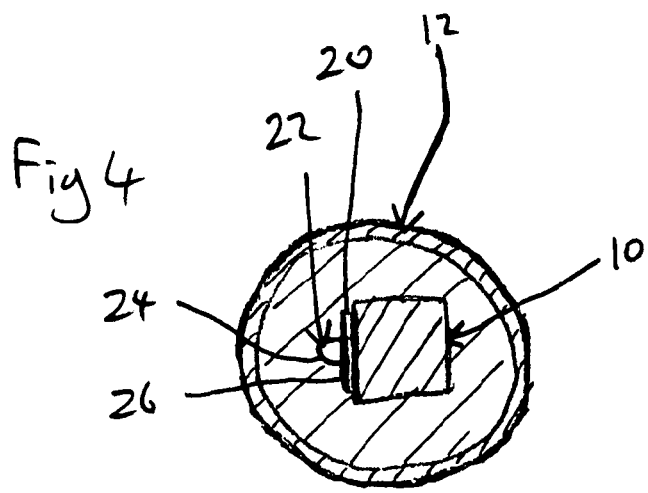
FIG. 4 is a view along the lines IV-IV in FIG. 3.
Figure 5:
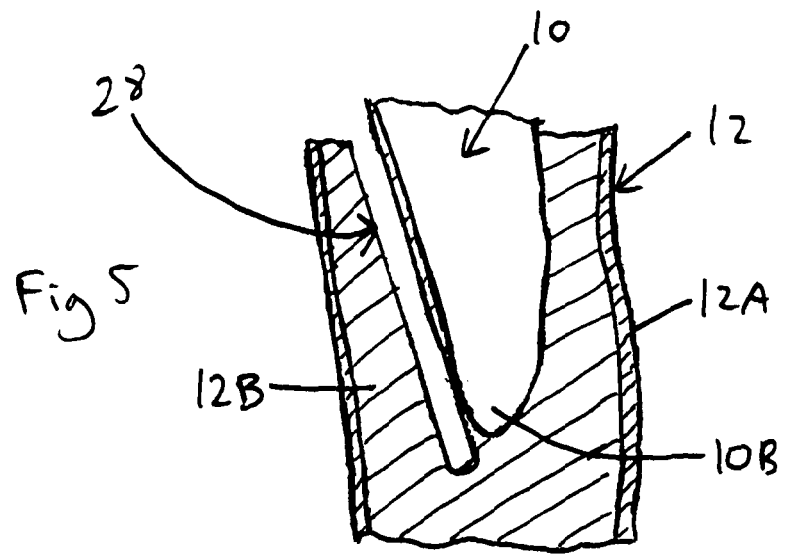
FIG. 5 shows a distal end region of the implant, in which and access tunnel has been formed adjacent the implant.

Referring to FIGS. 3 and 4, the next stage in the process is shown, in which a drill guide 22 is provided. The drill guide 22 has a guide portion 24 through which a drill bit, such as a 3 mm drill bit, can be inserted. The drill guide 22 also has an insertion portion 26, which can be inserted into the recess 20 adjacent the anterior face 16 of the implant 10.

With the drill guide 22 held in the position shown in FIGS. 3 and 4, an access tunnel 28 (see FIG. 5) is formed in the cancellous the bone tissue 12B immediately adjacent the anterior face 16 of the implant 10. A 3 mm access tunnel 28 is formed by the insertion of a 3 mm drill bit, through the guide portion 24 and into the cancellous bone tissue 12B.

The access tunnel 28 is formed by drilling through the cancellous bone tissue 12B to a region just beyond the distal end 10B of the implant 10. When the access tunnel 28 has been formed, and the drill bit removed, a cavity forming apparatus 30 is inserted into the access tunnel 28 in the direction as shown by the arrow X.

Figure 6:
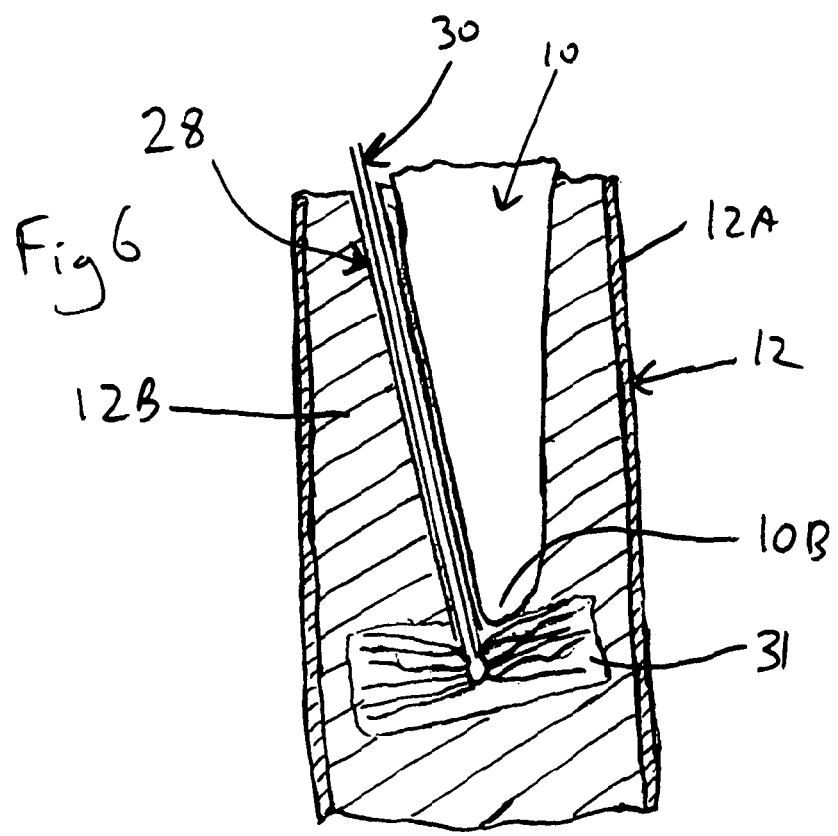
FIG. 6 shows a cavity being formed by a cavity forming apparatus.

FIG. 6 shows the situation after the cavity forming apparatus 30 has formed a cavity 31 beyond the distal end 10B of the implant 10.

Figures 7, 8:
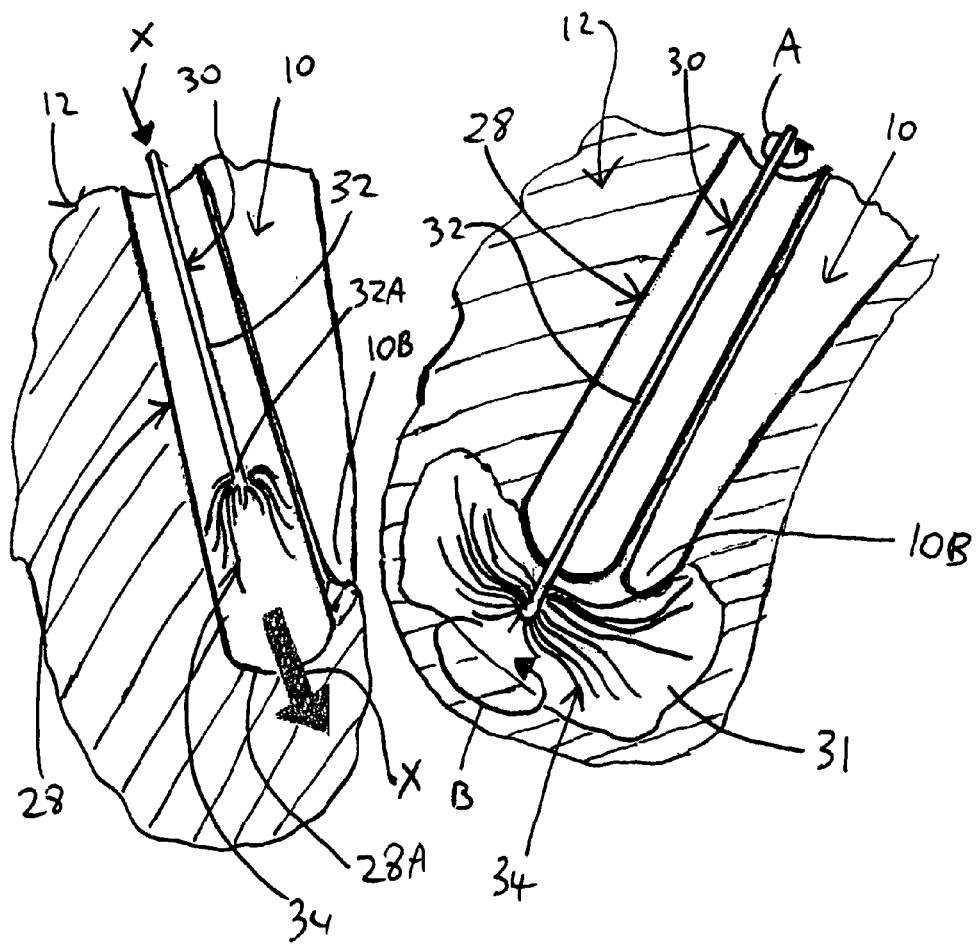
FIG. 7 shows the insertion of the cavity forming apparatus through the access tunnel.
FIG. 8 shows the formation of the cavity beyond the distal end of the implant.

FIGS. 7 and 8 show the steps of forming the cavity 31 beyond the distal end 10B of the implant 10. As can be seen from FIGS. 7 and 8, the cavity forming apparatus 30 comprises a the torque transmission member, in the form of an elongate shaft 32, having at the distal end 32A thereof a cavity forming means 34 comprising a plurality of spines, bristles or wires.

The cavity forming apparatus 30 is inserted into the access tunnel 28 until it reaches the distal end 28A thereof, at which stage, the shaft 32 is rotated as indicated by the arrow A. This causes the cavity forming means 34 to rotate as shown by the arrow B.

The rotation of the cavity forming means 34 causes the spines, bristles or wires to rub against the cancellous bone tissue at the side of the access tunnel 28, thereby wearing away the cancellous bone tissue. This process continues until the cavity 31 is formed. A saline solution can be flushed into the cavity 31, and suction can be used to remove debris from the cavity 31.

The cavity forming means 34 is then removed by withdrawing it from the access tunnel 28 in the direction opposite to the arrow X.

The delivery arrangement 36 is then inserted into the access tunnel 28. The delivery arrangement 36 is shown in FIGS. 9 to 13, and comprises a tubular housing 38, which is hollow, defining an elongate space 40. The space 40 extends the length of the tubular housing 38.

The tubular housing 38 has a distal end 42, which has a pointed distal end region. The pointed distal end 42 facilitates insertion of the housing 38 into the access tunnel 28. A delivery aperture 43 is defined at the distal end 42.

The delivery arrangement 36 also includes a delivery member 44 which comprises an elongate portion 46, which can extend the length of the housing 38. At the distal end of the elongate portion 46, there is provided a pair of co-operating members 48, 50, which are integrally formed with the elongate portion 46.

The co-operating members 48, 50 are formed of a resilient material and are urged by the resilience of the material from a retracted position, as shown in FIG. 12 to an expanded position shown in FIG. 13. The co-operating members may comprise a forked arrangement. When the co-operating members are in the expanded position, the co-operating members may fork away from each other. The purpose of this is explained below.

Each of the co-operating members 48, 50 is provided at its free end with a hook element 52, which can hold a portion of a flexible elongate cutting member 54. Published international patent specification number WO 2009/027642 discloses a suitable cutting apparatus for use in the method described herein. The cutting apparatus utilises a flexible elongate member for cutting around previously implanted surgical implants. The cutting apparatus disclosed in WO 2009/027642 delivers a flexible elongate cutting member continuously to effect the cutting around an implant.

As can be seen from FIGS. 12 and 13, the flexible elongate cutting member 54 is arranged such that a portion 56 thereof is looped between the two hook elements 52 of the respective co-operating members 48, 50. The flexible elongate cutting member 54 extends from the torque and 52 alongside the elongate portion 46 to a driver provided to drive the flexible elongate cutting member 54 along its length.

In use, the elongate delivery housing 38 is inserted into the access tunnel 28, until the access aperture 43 defined in the delivery housing 38 reaches the cavity 31 formed beyond the distal end 10B of the implant 10. In this position, the access aperture 43 faces towards the region just beyond the distal end 10B of the implant 10, for reasons that will be explained below.

The flexible elongate cutting member 54 is arranged such that the loop 56 extends between the two hook elements 52. The co-operating members 48, 50 are pushed to the retracted position, and the delivery member 44 is inserted into the housing 38 via an axial insertion aperture (not shown) at the proximal end of the housing 38.

The delivery member 44 is pushed into the housing 38 via the insertion aperture with the co-operating members 48, 50 leading. The co-operating members 48, 50 are pushed down the housing in the direction of the arrow Y until the co-operating members 48, 50 are pushed out of the access aperture 43.

As soon as the co-operating members 48, 50 are pushed out of the access aperture 43, the co-operating members 48, 50 move to the expanded position, in which the co-operating members fork away from each other, as shown in FIG. 13. The loop 56 is now in a suitable position to loop around the distal end 10B of the implant 10.

The loop 56 may be formed of a smoother material than the remainder of the flexible elongate cutting member 54. It is desirable that approximately 20 cm of the length of the flexible elongate cutting member is formed of the smooth material. This facilitates the insertion of the flexible elongate member into the housing 38 and the looping of the loop 56 around the distal end 10B of the implant 10.

The cutting apparatus is described in detail in WO 2009/027642, and is described briefly below.

Figure 14:
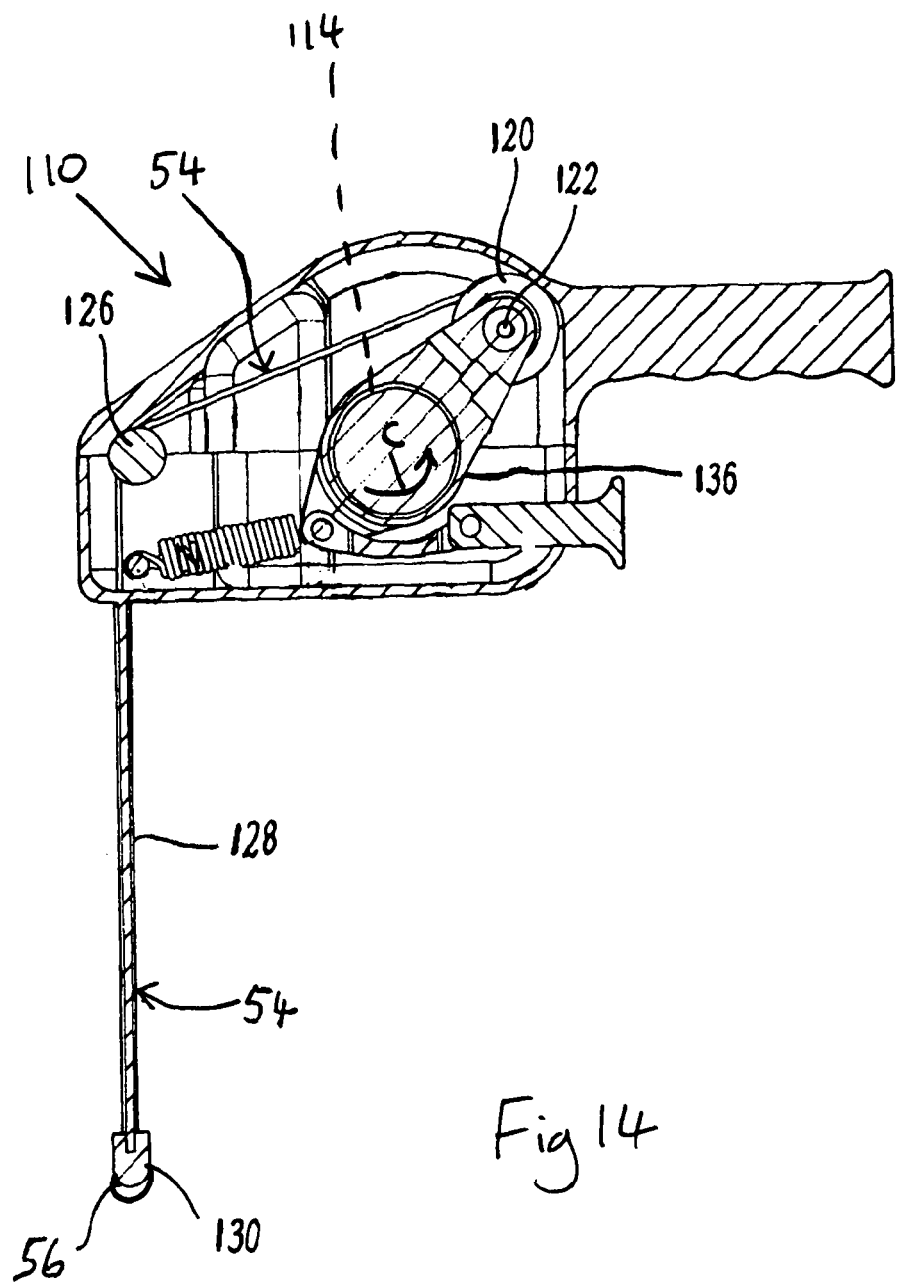
FIG. 14 is a side view of a cutting device showing internal components.

Referring to FIG. 14, the internal mechanism of a cutting apparatus 110 is shown. The cutting apparatus 110 is suitable to be used to cut bone material or cement that surrounds a stem of, for example, an implant used in total hip arthroplasty.

The cutting apparatus 110 comprises the flexible elongate cutting member 54 in the form of a cutting wire, spring, cable or chain which, in the embodiment shown, is endless. The flexible elongate member 54 is arranged on a tensioning arrangement comprising a rotary member in the form of a drum 114 held within a housing 136 The flexible elongate member 54 is wound circumferentially around the drum 114 in a plurality of coils that extend adjacent one another across the drum 114.

Roller members in the form of first and second jockey wheels 120 are provided adjacent the drum 114. The first and second jockey wheels 120 are freely rotatable on an axle held in an axle sleeve 122. The flexible elongate member 54 extends from the drum 114 to the one of the first and second jockey wheels 120 and then to a guide member 126.

The guide member 126 is cylindrical in configuration and has two circumferentially extending guide recesses defined therein to receive the flexible elongate member 54.

The flexible elongate member 54 extends from the guide member 126 to one of two guide conduits, comprising two guide tubes in the form of elongate tubular cable housing sheaths 128. The flexible elongate member 54 extends from the cable housing sheath 128 to a nozzle 130. The recesses in the guide member 126 are positioned to guide the flexible elongate member 54 into the cable housing sheaths 128.

A loop 56 of the flexible elongate member 54 extends forwardly of the nozzle 130, and the flexible elongate member 54 extends from the loop 56 through the nozzle 130 and the other of the two cable housing sheaths 128 back to the guide member 126, at the other of the two recesses. The nozzle 130 is provided to orient the flexible elongate member 54 as it passes from the cable housing sheath 128.

The flexible elongate member 54 extends from the guide member 126 to the other of the first and second jockey wheels 120, and the flexible elongate member 54 extends therefrom to the drum 114. Thus, by rotating the drum 114 in the direction indicated by the arrow C, the flexible elongate member 54 moves lengthwise.

When the loop 56 of the flexible elongate member 54 is arranged around the distal end 10B of the implant 10, the flexible elongate member can be driven along its length to cut through the cancellous bone tissue 12B surrounding the implant 10.

In use, the loop 56 is curved outwardly from the nozzle 130 and hooked onto the hook elements 52 on the first and second co-operating members 48, 50. The flexible elongate member 54 is then arranged to extend along the elongate portion 46 of the delivery member 44. The delivery member 44 is then inserted into the tubular housing 38 until the co-operating members 48, 50, with the flexible elongate member 54 hooked thereon, reaches the delivery aperture 43.

The delivery arrangement 36 is then inserted into the access tunnel 28, until the delivery aperture 43 reaches the cavity 31. The delivery member 44 is then pushed so that the co-operating members 48, 50 are moved out of the aperture 43 and snap immediately to the forked expanded position, shown in FIG. 13. In this position, the loop 56 of the flexible elongate member 54 is looped around the distal end 10B of the implant 10. The tubular housing 38 and the delivery member 44 are then withdrawn out of the access tunnel 28.

The tubular cable housing sheaths 128 are then pushed along the flexible elongate member 54 until the nozzle 130 is disposed just adjacent the distal end 10B of the implant 10.

The cutting apparatus 110 is then activated to drive the flexible elongate member 54 along its length. When the cutting portion of the flexible elongate member 54 engages the cancellous bone tissue 12B the cable housing sheaths 128, with the nozzle 130, are withdrawn from the access tunnel 28.

The loop 54 extending around the implant 10 is dragged along the implant 10. This has the effect that the cutting portion of the flexible elongate member 54 cuts through the cancellous bone tissue 12B around the implant 10 as the flexible elongate member is moved from the distal end 10B to the proximal end 10A of the implant 10. When the cutting of the cancellous bone tissue 12B is complete, the implant 10 can be removed from the bone.

A further embodiment is shown in FIGS. 15 to 18, in which, the implant 10 is secured within the bone 12 by a cement mantle 60. The cement mantle 60 extends from the proximal end 10A, beyond the distal end 10B of the implant 10 to a cement restrictor 62.

With such an implant 10, it is necessary to remove the cement mantle 60 as well as the implant 10. This is effected by the provision of a plurality of elongate guide members 64, in the form of K-wires, as described below.

The access tunnel 28 is first drilled down into the bone 12 at the junction 65 between the cement mantle 60 and the cancellous bone tissue 12B, in the same way as described above with reference to FIGS. 1 to 5. The access tunnel 28 is drilled so that it extends beyond the cement restrictor 62.

The cavity forming apparatus 30 is then inserted into the access tunnel 28 to form a cavity 31 beyond the cement restrictor 62. The cavity 31 is formed in the same manner as the cavity 31 described above with reference to FIGS. 6, 7 and 8.

A plurality of elongate bores 66 are then formed at the junction 65 between the cement mantle 60 and the cancellous bone tissue 12B. Each elongate bore 66 is substantially 2 mm in diameter, and extends longitudinally of the bone 12 along the cement mantle 60. The elongate bores 66 are spaced from the one another around the junction 65 between the cement mantle 60 and the cancellous bone tissue 12B.

The elongate bores 66 extend from the proximal end 10A of the implant 10 to the cavity 31 beyond the cement restrictor 62. A respective one of the guide members 64 is then inserted into each of the elongate bores 66. The guide members 64 form a cage around the cement mantle 60. Each guide member 64 has a proximal end portion 64A and a curved distal end portion 64B.

Each guide member 64 is arranged in the respective elongate bore 66 so that the curved distal end portions 64B of the guide members 64 converge inwardly towards each other. The number of guide members 64 can be between five and seven.

Figure 17:
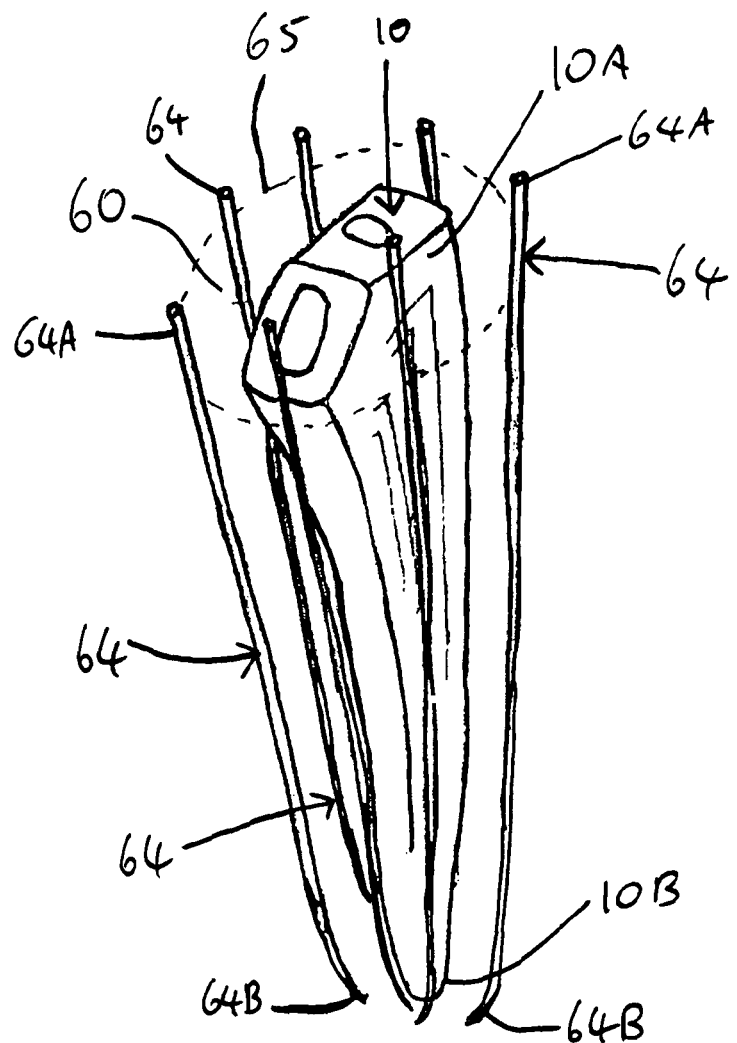
FIG. 17 shows an implant enclosed by the enclosing wires.
Figure 18:
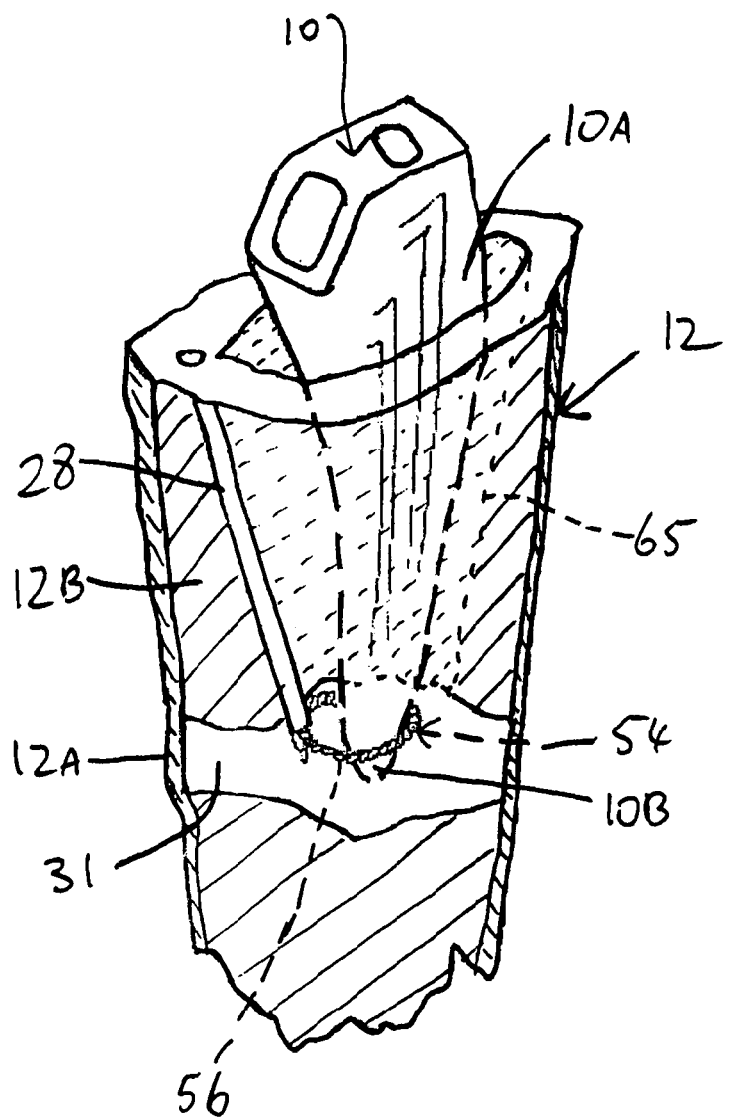
FIG. 18 shows a step of cutting around the implant.

FIG. 17 shows the arrangement of the guide members 64 around the implant 10 at the junction 65 of the cement mantle 60 and the cancellous bone tissue 12 be. In order to depict clearly the arrangement of the guide members 64, the bone 12 is not shown in FIG. 17.

The flexible elongate member 54 is then delivered to the cavity 31 along the access tunnel 28, in the same way as described above, but in the embodiment shown in FIGS. 15 to 18, the loop 56 held by the co-operating members 48, 50 is delivered by the delivery member to the distal end portions 64B of the guide members 64. The loop 56 is looped around the distal end portions 64A of the guide members 64.

The delivery arrangement 38 is withdrawn from the access tunnel 28, and the cable housing sheaths 126 inserted therein over the flexible elongate member 54 until the nozzle 130 is disposed just adjacent the distal end portions 64A of the guide members 64.

The cutting apparatus 110 can then be activated and the flexible elongate member 54 driven along its length to cut the cancellous bone 12B surrounding the cement mantle 60.

The flexible elongate member 54 is then withdrawn from the access aperture 28, with the cable housing sheaths 126 and the nozzle 130. This drags the loop 56 along the guide members 64 to cut the cement mantle 60 from the cancellous bone 12B, so that the implant 10 and the cement mantle 60 can then be removed from the bone 12.

Figure 19:
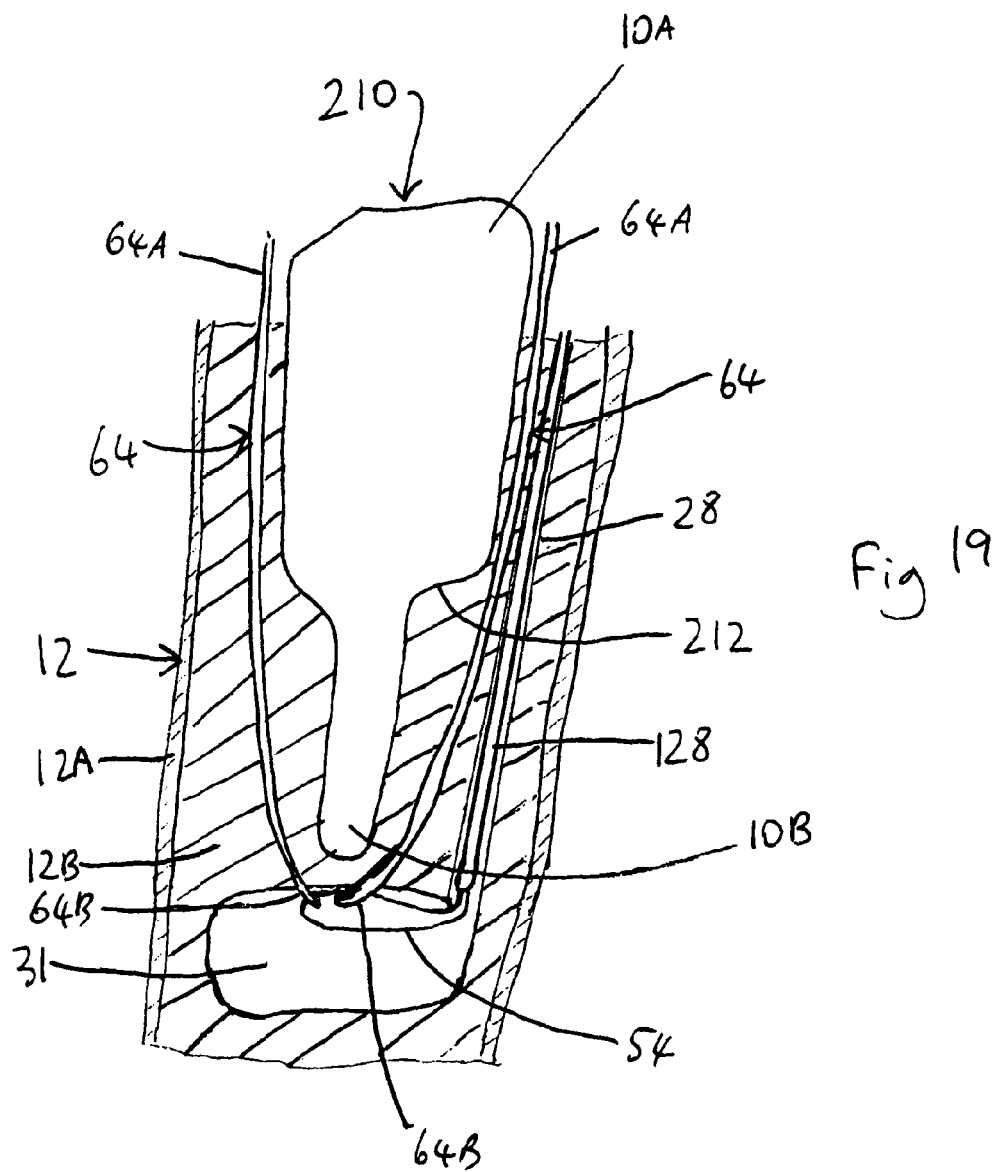
FIG. 19 shows the use of enclosing wires with an embedded article having a stepped configuration.

Various modifications can be made without departing from the scope of the invention. For example, FIG. 19 shows a method for removing an implant 210, having a proximal end 210A and a distal end 210B. The proximal end 210A is wider than the distal end 210B, and a step 212 is provided between the proximal and distal ends 210A, 210B.

A plurality of the guide members 64 are provided around the implant 210 in generally the same way as described above. An access tunnel 298 and a cavity 31 are formed, also in the same way as described above. The cutting member 54 is arranged around the distal ends 64B of the guide members 64 using the delivery member 36 described above, and the cutting member 54 extends through housing sheaths 128 in the access tunnel 28.

The guide members 64 are provided to guide the cutting member passed the step 212, and thereby prevent the cutting member 54 from becoming snagged on the step 212. Thus, the cutting member is driven to cut through the bone tissue 12B, by being pulled from the distal ends 64B of the guide members 64 to the proximal ends 64A, thereby cutting the embedded article 210 free from the bone tissue 12B.

A further modification is shown in FIGS. 20 and 21, two access tunnels, designated 28A and 28B are drilled adjacent the implant 10. The cavity 31 is formed in the manner described above by the insertion of the cavity forming apparatus 30 (not shown in FIG. 20 or 21) into one of the first access tunnel 28A. FIG. 21 shows the cavity 31 in broken lines.

It will be appreciated that the first and second access tunnels 28A and 28B can both be formed prior to the formation of the cavity 31, in which case, the cavity 31 can be formed by the insertion of the cavity forming apparatus into either of the first and second access tunnels 28A, 28B.

Alternatively, one of the first and second access tunnels 28A, 28B can initially be formed, and then the cavity 31 can be formed. The second access tunnel 28B can be formed after the formation of the cavity 31.

A first end portion of the elongate flexible cutting member 54 is inserted into the cavity 31 via the first access tunnel 28A, and a second end portion of the elongate flexible cutting member 54 is inserted into the cavity 31 via the second access tunnel 28B.

The first and second end portions may be opposite and portions of the same cutting member 54.

The first and second end portions of the cutting member 54 have corresponding cooperating formations which can cooperate with each other to connect the first end portion to the second end portion. This allows the connected first and second end portions of the cutting member 54 to be pulled through one of the first and second access tunnels 28A, 28B, and a more thorough connection effected between the first and second end portions outside the femur 12.

The cutting member 54 extends across a first region 10C of the implant 10. The cutting member 54 can then be driven along its length to cut the bone tissue away from the first region 10 of the implant 10 by being pulled, as described above from the distal end 10B to the proximal end 10A thereof.

Subsequently, the first and second portions of the cutting member 54 are separated from each other and then inserted back into the first and second access tunnels 28A, 28B respectively, to be reconnected to each other in the manner described above.

The cutting member 54 is then manipulated so that it extends across a second region 10D of the implant 10, as shown in broken lines in FIG. 20. The cutting member 54 can then be driven lengthwise and pulled from the distal end 10B to the proximal end 10A of the implant to cut the bone tissue away from the second region 10D of the implant.

When the first and second regions 10A, 10B have been cut from the bone tissue in the manner described above, the implant can then be removed from the femur 12.

Further modifications are shown in FIGS. 22 to 39, which show a drill guide 150, a surgical apparatus 250 for forming a cavity, and a delivery device 350.

An embodiment of a drill guide 150 is shown in FIGS. 22 to 29. The drill guide 150 comprises a mounting arrangement 152 to mount the drill guide 150 on a projection 154 of a femoral implant 156.

The drill guide 150 further includes a holding arrangement 158 for holding first and second drills 160, 162, in the form of K-wires.

The mounting arrangement 152 comprises a mounting member 164 which defines a bore 156 therethrough. The projection 154 on the implant 156 is received in the bore

166. A shim 168 is provided in the bore 166 between the inner surface of the bore 166 and the projection 154. A bolt 170 is threadably received in a threaded aperture in the mounting member 164 and engages the projection 154 on the implant 156 to secure the mounting member to the implant 156. The shim 168 defines a slot through which the bolt 170 extends to engage the projection 154. The slot allows adjustment of the position of the shim 168 relative to the mounting member 164.

The holding arrangement 158 comprises first and second holding members 172, 174 which are arranged to hold first and second guide arrangements 176, 178.

Each of the holding members 172, 174 has an H-shaped profile and each has a respective first region 180, 182 to hold the first guide arrangement 176, and a respective second region 184, 186 to hold the second guide arrangement 178.

FIGS. 24 and 25 show the first holding member 172. An attaching member 188 extends from the first holding member 172 and is provided to attach the mounting arrangement 152 to the first holding member 172. The attaching member 188 defines a pair of substantially parallel slots 190, 192, through which screws 194 extend. The screws 194 are threadably received in respective threaded apertures in the mounting member 164. The screws 194 are tightened against the attaching member 188 to attach the holding member 172 to the mounting member 164.

The holding arrangement 158 further includes a tightening means 196 to tighten the first and second holding members 172, 174 onto the first and second guide arrangements 176, 178. Each guide arrangement 176, 178 comprises a guide member in the form of a guide tube 198 and a spheroidal adjustment member 200 arranged centrally on the guide tube 198.

Each of these spheroidal adjustment members 200 is clamped between the first and second holding members 172, 174 at the respective first regions 180, 182 or at the respective second regions 184, 186. This holds the first and second guide arrangements 176, 178 in a desired position. The tightening means 196 tightens the first and second holding members 172, 174 onto the spheroidal adjustment members 200.

Referring to FIG. 29, the tightening means 196 comprises a first tightening member in the form of an inner elongate member 202 which is fixedly attached to the first holding member 172, and extends upwardly therefrom through an aperture 203 in the second holding member 174. The inner elongate member 202 is externally threaded at a distal region 206 spaced from the second holding member 174.

The tightening means further includes a second tightening member in the form of an outer tubular member 208, which is arranged overly in an elongate member 202 so that the outer tubular member 208 engages the second holding member 174. The outer tubular member 208 has an internally threaded region 210 which threadably engages the distal region 206 of the inner elongate member 202. Thus, the outer tubular member 208 can be screwed onto the inner elongate member 202 and thereby tighten the first and second holding member 172, 174 onto the spheroidal adjustment members 200. This has the effect of holding the first and second guide arrangements 176, 178 in a desired position. The position of the first and second guide arrangements 176, 178 can be adjusted by unscrewing the outer tubular member 208 from the inner elongate member 202 to release the spheroidal adjustment members 200.

Each guide arrangement 176, 178 includes securing means 212 to secure the guide arrangements 176, 178 to the holding arrangement 158. The securing means 212 comprises a securing portion 214 defining a slot 215 therethrough, and a connecting portion 216 to connect the securing portion 214 to the respective guide member 198. In order to secure the securing portions 214 to each other and to the holding arrangement 158, the slots 215 overlap each other and a fastening member 220 is inserted therethrough to be secured to an upstanding securing member 218, as explained below.

The holding arrangement 158 further includes the upstanding securing member 218 on the second holding member 274. The upstanding securing member 218 defines a threaded aperture 219 (see FIG. 29). The fastening member 220 is in the form of a screw or a bolt and extends through the overlapping slots 215 in securing portions 214. The fastening member 218 is threadably received in the threaded aperture 219 so that the securing portions 214 and the guide arrangements 176, 178 are secured to each other and to the holding arrangement 158.

In use, the outer tubular member 208 is released from the inner elongate member 202, and the fastening member 220 is released from the upstanding securing member 218. This releases the first and second guide arrangements 176, 178 and allows them to be pivoted about the spheroidal adjustment members 200. The holding arrangement 158 is thus in a release condition.

The drills 160, 162 are inserted into the guide members 198, and the positions of the first and second guide arrangements 176, 178 are adjusted until a position is reached where the drill tips of the drills 160, 162 extend just beyond the lower end of the surgical implant 156. A marker (not shown) can then be disposed on the drills 160, 162, to mark their position, so that the surgeon will know when the tips of the drills 160, 162 are at the region beyond the distal end of the implant.

The outer tubular member 208 is then retightened onto the inner elongate member 202, and the fastening member 220 is screwed back into the upstanding securing member 218, to lock the various components of the holding arrangements 158 in position. The holding arrangement 158 is thus in a holding or locked condition.

The screw 170 can then be removed from the projection 154 to allow the drill guide 150 to be removed from the implant 156.

The drill guide 150 can then be arranged on the identical implant in the bone of a patient, the drills 160, 162 having been previously removed.

The drills 160, 162 are then inserted into the guide members 198 again, and thereafter into the bone of the patient adjacent the implant 156. This insertion is carried out by rotating the drills 160, 162 about their longitudinal axes to remove cancellous bone, thereby drilling tunnels into the bone on opposite sides of the implant 156. When the markings on the respective drills 160, 162 reach their predetermined position, the surgeon will know that tunnels have been drilled into the bone to the region just beyond the distal end of the implant 156.

FIGS. 30 to 34 show a surgical apparatus 250 for forming a cavity in the cancellous bone of a femur beyond the distal end of an implant.

The surgical apparatus 250 comprises a cavity forming arrangement 252, and a moveable housing arrangement 254 for housing the cavity forming arrangement 252. The surgical apparatus 250 also includes a drive arrangement in the form of a rotatable barrel 256 for driving the housing arrangement 254 on rotation of the barrel 256. The surgical apparatus 250 further includes an anti-rotation arrangement 257 to prevent rotation of the cavity forming arrangement 252 on rotation of the barrel 256.

Figure 31:
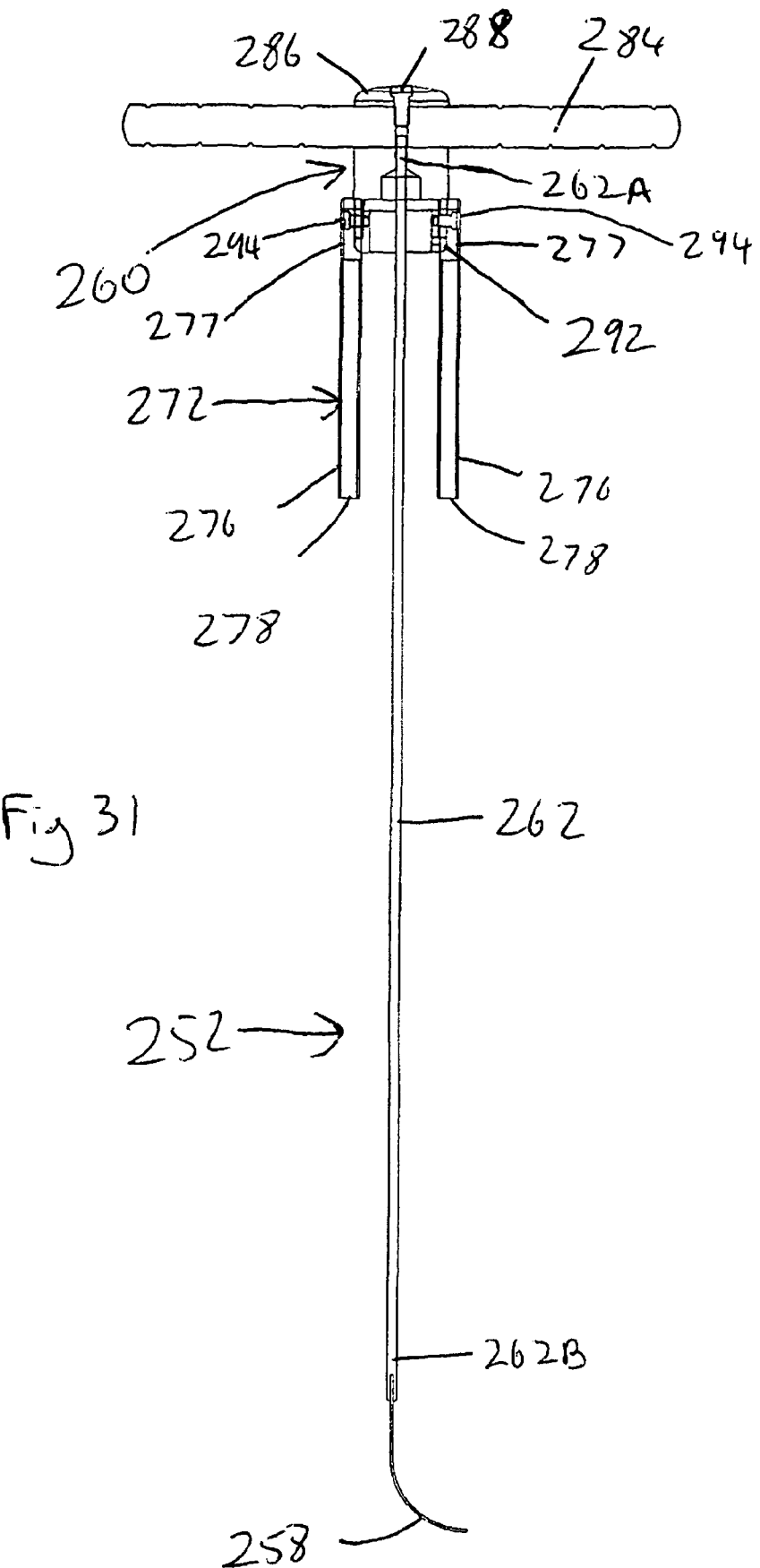
FIG. 31 is a front view of a cavity forming arrangement for use in the surgical apparatus shown in FIG. 30.

The cavity forming arrangement 252 is shown in FIG. 31 and comprises a cavity forming element 258 formed of flexible metallic material, a manipulating assembly 260 for manipulating the surgical apparatus 250, and an elongate shaft 262 extending between the cavity forming element 258 and the manipulating assembly 260. The shaft 262 has a proximal end 262A and a distal end 262B, with the cutting member being mounted at the distal end 262B of the shaft 262. The manipulating assembly 260 is mounted at the region of the proximal end 262A of the shaft 262.

Figure 32:
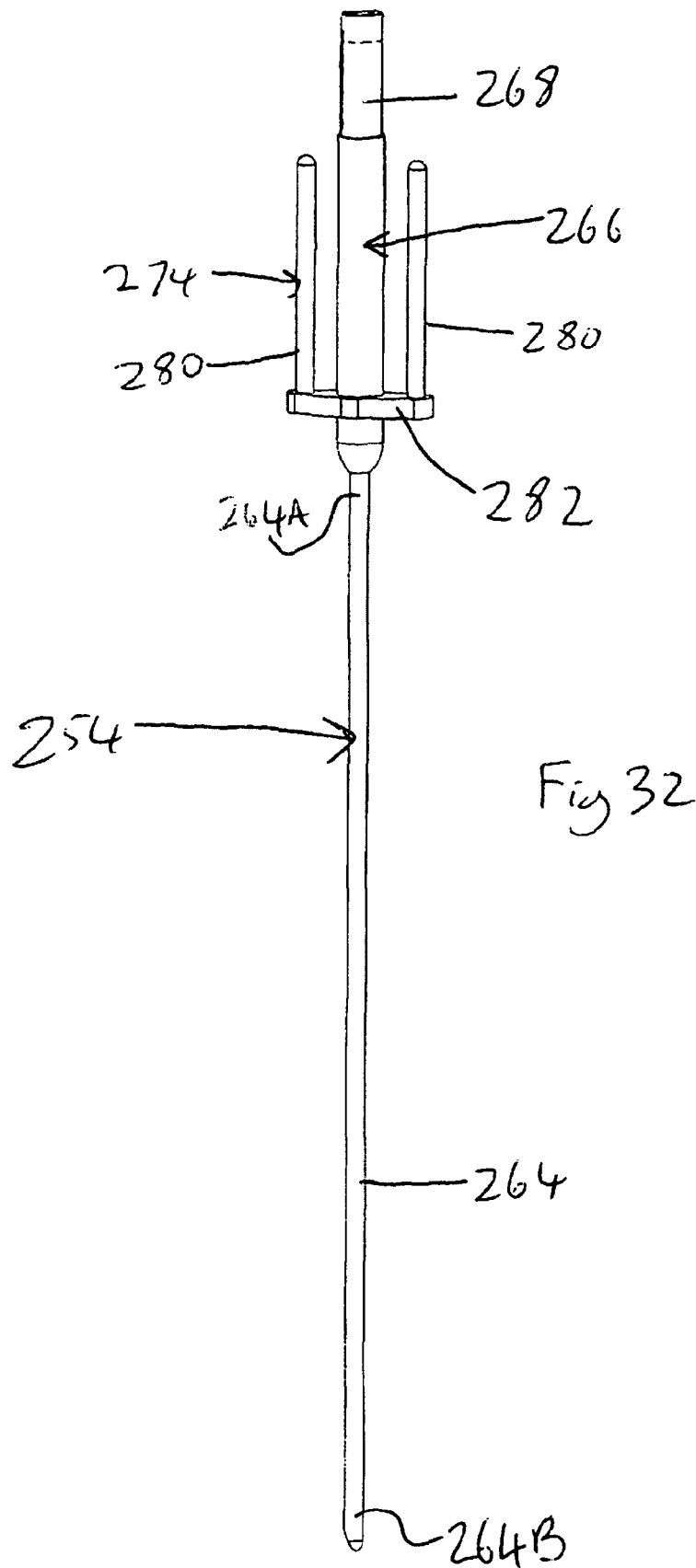
FIG. 32 is a front view of a housing arrangement for use in the surgical apparatus shown in FIG. 30.

The housing arrangement 254 is shown in FIG. 32 and comprises an elongate tubular portion 264 having an open proximal end 264A and an open distal end 264B. The shaft 262 extends through the elongate tubular portion 264 and the cavity forming element 258 extends from the opening in the distal end 264B of the elongate tubular portion 264.

The housing arrangement 254 includes a tubular threaded member 266 provided on the elongate tubular portion 264 at the proximal end 264A thereof. The tubular threaded member 266 includes an externally threaded region 268 to co-operate with internal threads on the rotatable barrel 256, as explained below.

The surgical apparatus 250 further includes an anti-rotation arrangement 270 to prevent rotation of the cavity forming arrangement 252 relative to the housing arrangement 254 during operation.

The anti-rotation arrangement 270 comprises a first part 272 fixedly mounted on the cavity forming arrangement 252, and a second part 274 fixedly mounted on the housing arrangement 254.

The first part 272 of the anti-rotation arrangement 270 comprises a pair of first elongate elements in the form of elongate receiving elements 276. The elongate receiving elements 276 may comprise tubes, and extend from adjacent the proximal end of the shaft 262 towards the distal end. The elongate receiving elements 276 extend parallel to the shaft 262, with the shaft 262 being arranged therebetween. Each of the elongate receiving elements 276 has an open end 278 directed towards the distal end region of the shaft 262.

The second part 274 of the anti-rotation arrangement 270 comprises a pair of second elongate elements in the form of elongate insertion elements 280 extending alongside, and parallel to the tubular threaded member 266. As can be seen from FIG. 32, the tubular threaded member 266 is arranged between the elongate insertion elements 280.

Figure 33:
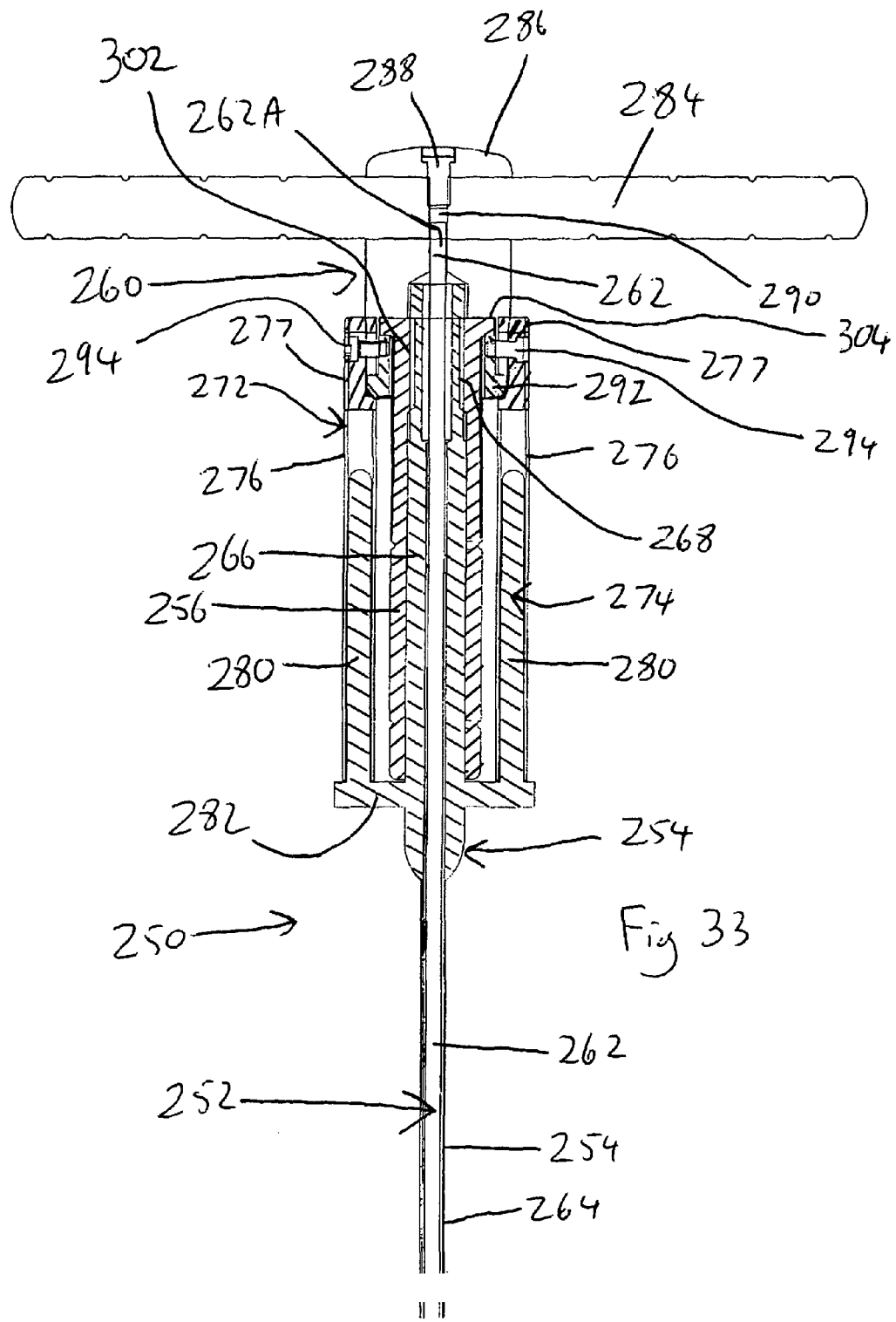
FIG. 33 is a close up sectional view of the region marked XXXIII in FIG. 30.

The anti-rotation arrangement 270 is shown more clearly in FIG. 33, which is a cross sectional view of the region marked XXXIII in FIG. 30. As can be seen from FIG. 33, the elongate insertion elements 280 are telescopically received in the elongate receiving elements 276. The elongate receiving elements 276 have proximal end regions 277 at which the elongate receiving elements are secured to the manipulating assembly 260. FIG. 33 also shows the manipulating assembly 260 in more detail. The manipulating assembly 260 comprises a handle 284 held by a cover member 286. A top screw 288 is threadably received in the handle 284 and secures the handle 284 to the cover member 286. The proximal end 262A of the shaft 262 is received in a recess 290 in the handle 284. A side screw 285 (see FIG. 30) extending through the cover member 286 engages the proximal end region 262A of the shaft 262 to secure the shaft 262 to the cover member 286. A bush 292 is provided at the distal end of the cover member 280 and is secured thereto by bush securing screws 294.

The bush securing screws 294 extend through the proximal end region 277 of the elongate receiving elements 276 to secure the elongate receiving elements 276 to the cover member 286 and to the bush 292. Thus, the first part 272 of the anti-rotation means 270 is fixed to the cavity forming arrangement 252. Similarly the second part 274 of the anti-rotation arrangement 270 is fixed to the housing arrangement 254.

Figure 34:
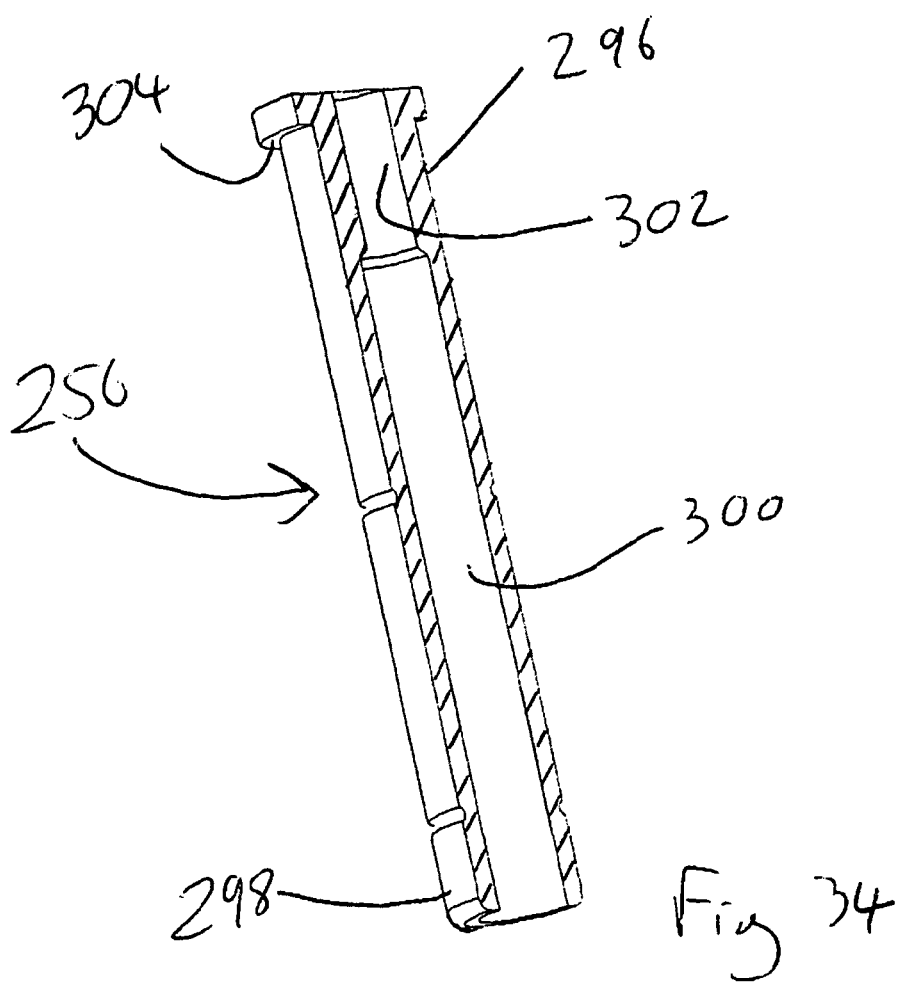
FIG. 34 is a sectional view in perspective of a barrel for use in the surgical apparatus shown in FIG. 30.
Figure 35:
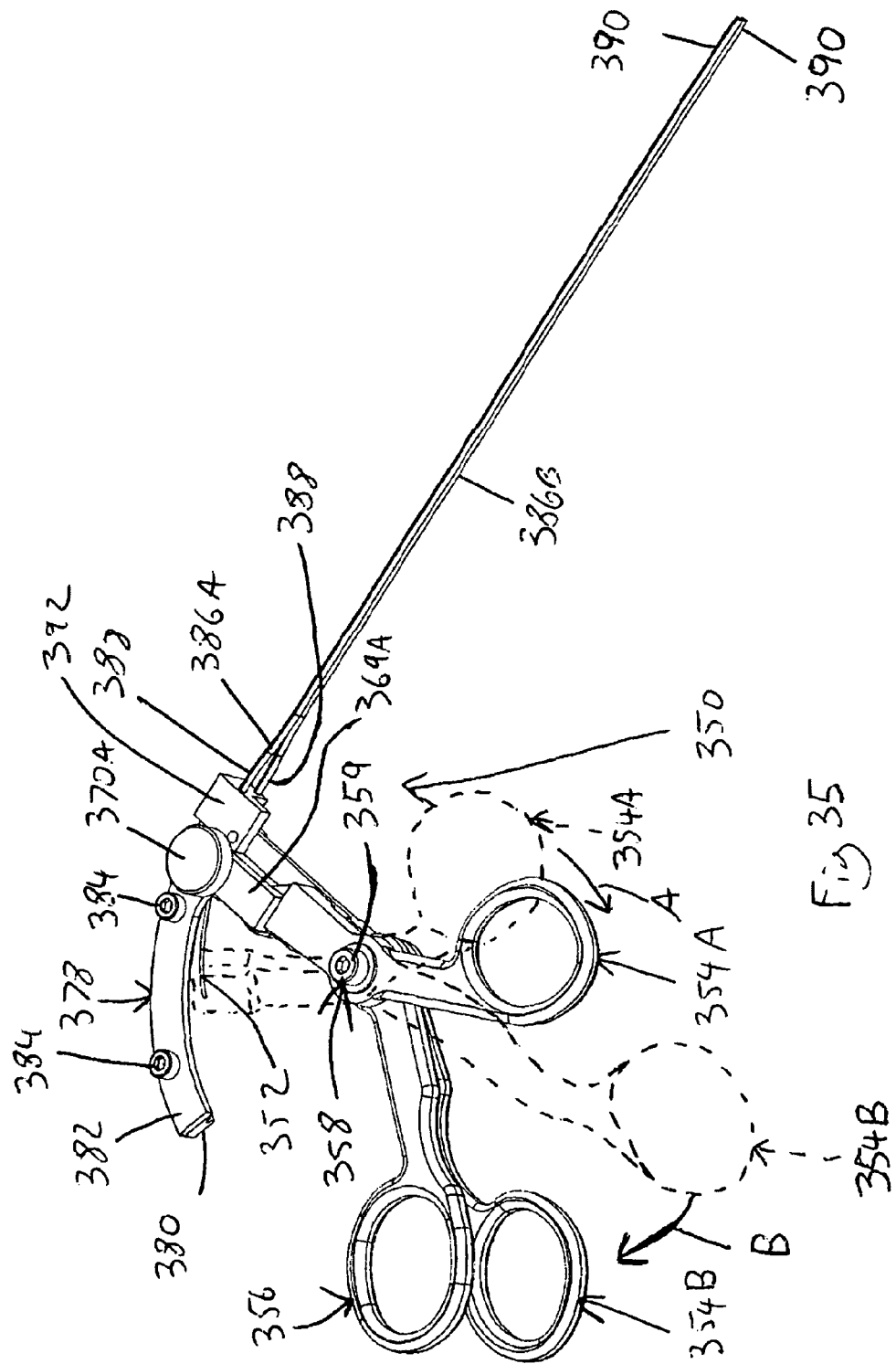
FIG. 35 is a view from one side of a delivery device.
Figure 36:
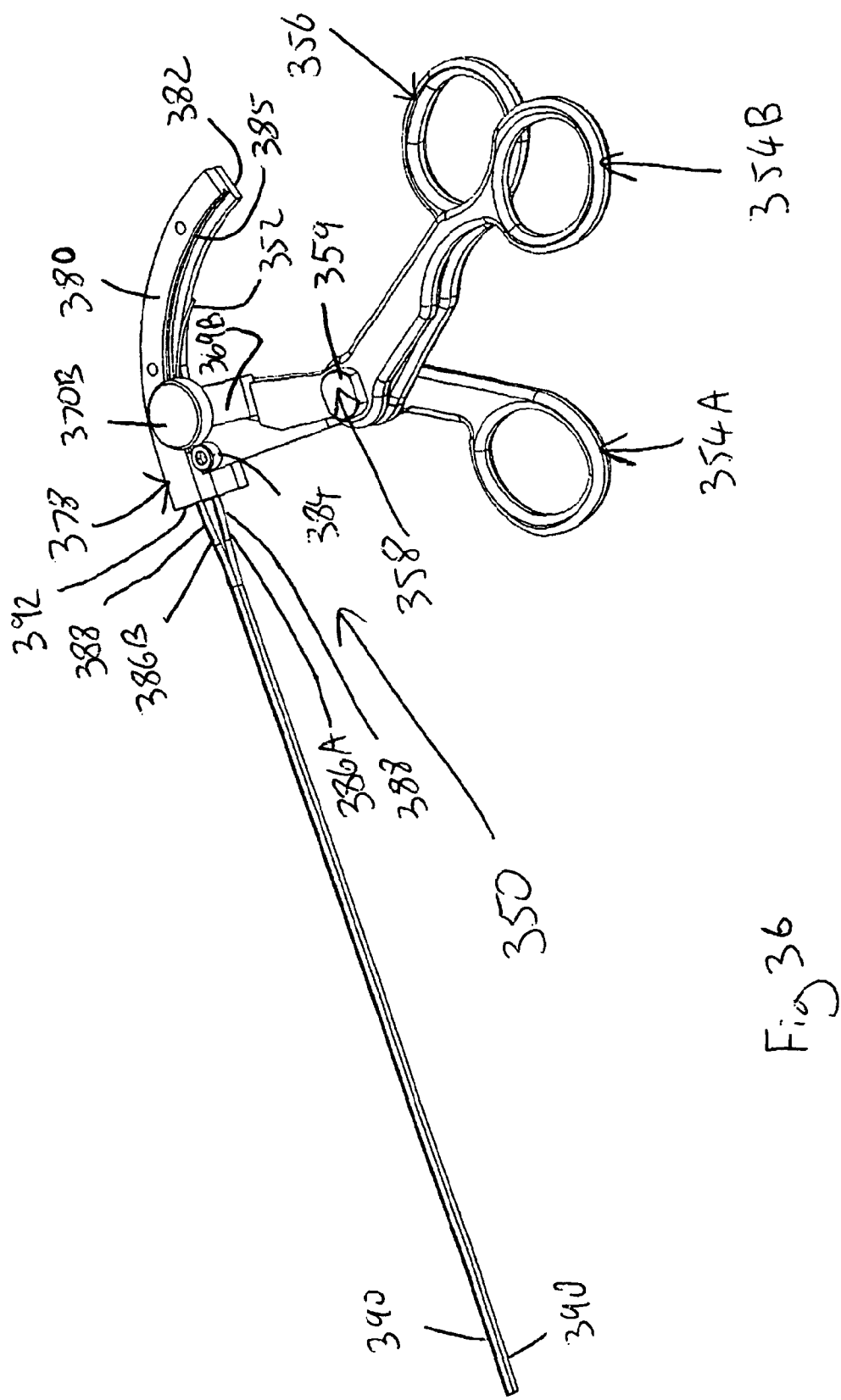
FIG. 36 is a view from the opposite side of the delivery device shown in FIG. 35.

A sectional view of the rotatable barrel 256 is shown in FIG. 34. The rotatable barrel 256 has a proximal end region 296 and a distal end region 298. The rotatable barrel 256 defines a bore 300 extending therethrough. The tubular threaded member 266 of the housing arrangement 254 extends through the bore 300 in the rotatable barrel 256. An internally threaded region 322 is provided at the proximal end region 296 of the rotatable barrel 256.

As can be seen from FIG. 33, the internally threaded region 302 of the rotatable barrel 256 threadably engages the externally threaded region 268 of the tubular threaded member 266. The rotatable barrel 256 has a radially outwardly extending flange 304 at the proximal end 296, which engages the bush 292 in the cover member 284. Thus, the bush 292 holds the rotatable barrel 256 in the cover member 286 by engaging the flange 304.

In operation, the surgical apparatus 250 is gripped by the handle 284, and the elongate tubular portion 264 with the shaft 262 and the cavity forming element 258 therein is inserted into one of the tunnels drilled in the bone adjacent the implant therein. The rotatable barrel 256 is rotated about its longitudinal axis, so that the threaded engagement between the rotatable barrel 256 and the tubular threaded member 266 drives the housing arrangement 254 in the direction indicated by the arrow A in FIG. 30, thereby revealing the cutting member 252 from its position inside the elongate tubular portion 264. As the cavity forming element 258 is revealed from the elongate tubular portion 264, it moves to a curved configuration, as shown in FIGS. 30 and 31. The position of the side screw 285 indicates the direction at which the cavity forming element 258 curves outwardly from the elongate tubular member 264. With the cavity forming element 258 fully revealed, the surgeon can manipulate the surgical apparatus 250 to create a cavity beyond the distal end of the implant.

When the surgeon is satisfied that the cavity has been created, the rotatable barrel 256 can be rotated in the opposite direction so that the housing arrangement 254 moves in the direction indicated by arrow B to cover the cavity forming element 258. When the cavity forming element 258 is received within the elongate tubular portion 264, it is held in a substantially straight configuration. The surgical apparatus 250 can then be withdrawn from the bone.

FIGS. 35 to 39 show a delivery device 350 for delivering an elongate wire cutter 352. The delivery device 350 comprises first and second delivery arrangements 354A, 354A and a support arrangement 356 for supporting the delivery arrangement 354A, 354B.

The first and second delivery arrangements 354A, 354A are pivotally mounted on the support arrangement 356 at a pivot 358, which comprises a pivot member 359 extending through the first and second delivery arrangement 354A, 354A and the support arrangement 356. As can be seen from FIGS. 35 and 36, the support arrangement 356 is disposed between the first and second delivery arrangements 354A, 354B.

Figure 37:
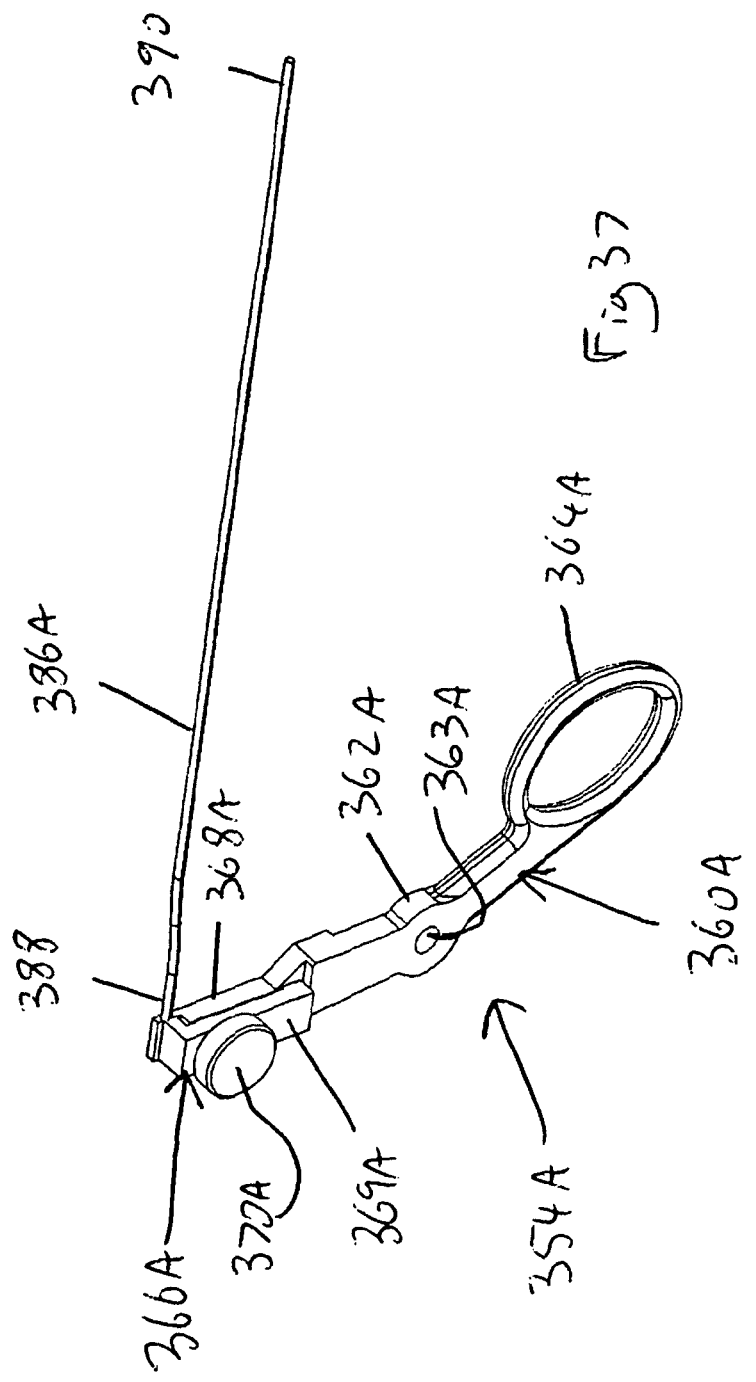
FIG. 37 is a side perspective view of a first delivery arrangement for use in the delivery device shown in FIG. 35.

The first delivery arrangement 354A is shown in FIG. 37 and comprises a first delivery member 360A having a first central pivot region 362A defining a first pivot aperture 363A through which the pivot member 359 extends. The first delivery arrangement 354A is pivotally mounted on the support arrangement 356 at the first pivot region 362A.

The first delivery arrangement 354A further includes a handle in the form of a first ring 364A into which a user can insert his or her thumb or finger to manipulate the first delivery arrangement 354A. The first ring 364A is provided on the first delivery member 360A on one side of the first pivot region 362A.

A first gripping assembly 366A is provided on the opposite side of the first pivot region 362A to the first ring 364A.

The purpose of the first gripping assembly 366A is to grip a first region of the elongate wire cutter 352 so that the elongate wire cutter 352 can be fed by the first delivery arrangement 354A.

First gripping assembly 366A comprises a fixed first gripping member 368A provided integrally on the first delivery member 360A, and a releasable first gripping member 369A fastened to the fixed first gripping member 368A. The releasable first gripping member 369A is substantially L shaped, and the fixed first gripping member 368A has a shoulder formation in which the shorter arm of the L shape releasable first gripping member 369A can be received.

A first fastening member 370A in the form of a first screw is provided to fasten the releasable first gripping member 369A to the fixed first gripping member 368A. The first fastening member 370A extends through the releasable first gripping member 369A and is threadably received in a threaded hole (not shown) in the fixed first gripping member 368A. The first region of the elongate cutting wire 352 can be disposed between the fixed and releasable first gripping members 368A, 369A and gripped thereby upon tightening the first fastening member 370A thereon.

Figure 38:
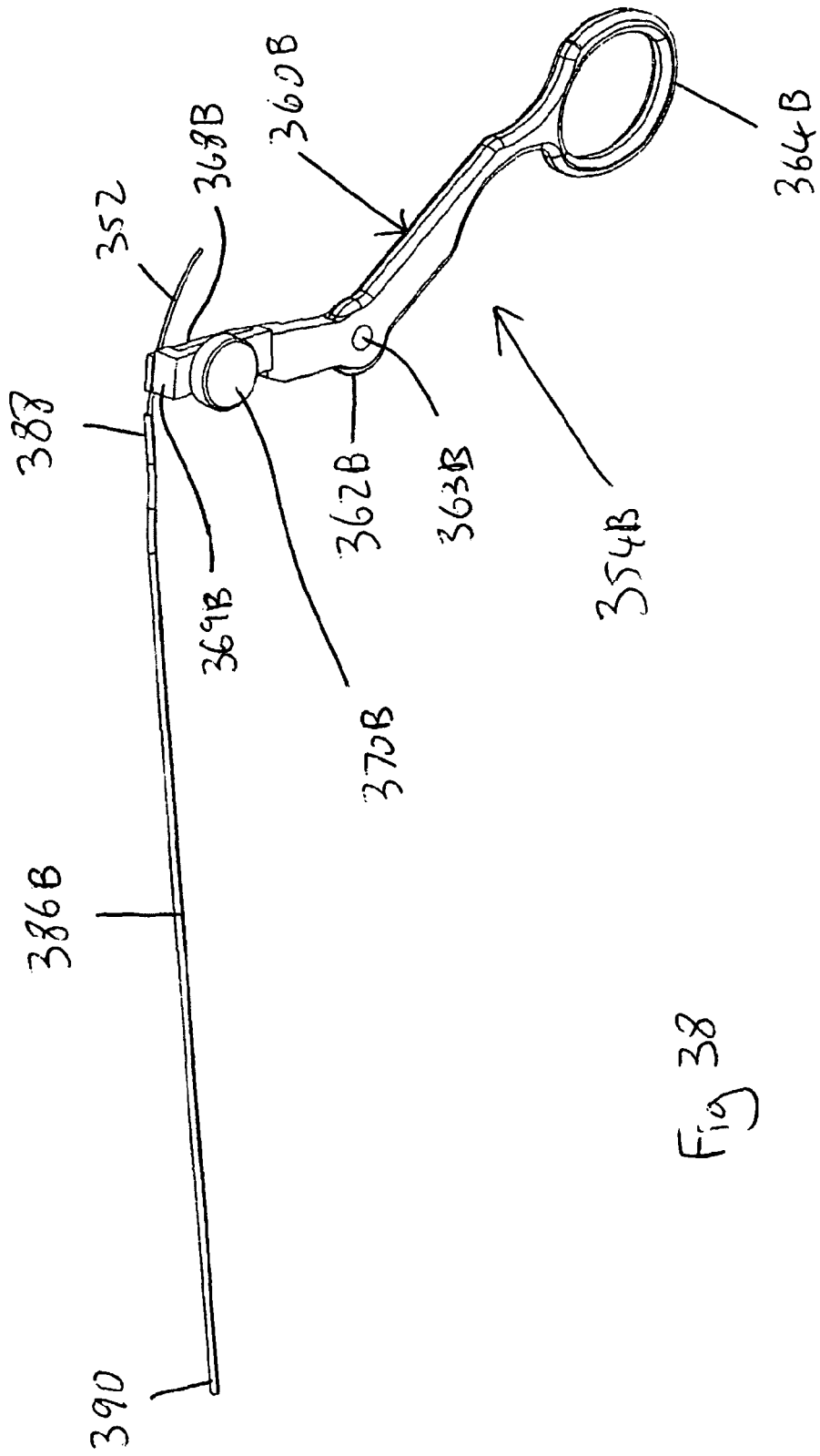
FIG. 38 is a side perspective view of a second delivery arrangement for use in the delivery device shown in FIG. 35.

The second delivery arrangement 354B is shown in FIG. 38 and comprises a second delivery member 360B having a second central pivot region 362B defining a second pivot aperture 363B through which the pivot member 359 extends. The second delivery arrangement 354B is pivotally mounted on the support arrangement 356 at the second pivot region 362A.

The second delivery arrangement 354B further includes a handle in the form of a second ring 364B into which a user can insert his or her thumb or finger to manipulate the second delivery arrangement 354A. The second ring 364B is provided on the second delivery member 360B on one side of the second pivot region 362B.

A second gripping assembly 366B is provided on the opposite side of the second pivot region 362B to the second ring 364B.

The purpose of the second gripping assembly 366B is to grip a second region of the elongate wire cutter 352 so that the elongate wire cutter 352 can be fed by the second delivery arrangement 354B.

Second gripping assembly 366B comprises a fixed second gripping member 368B provided integrally on the second delivery member 360B, and a releasable second gripping member 369B fastened to the fixed second gripping member 368A. The releasable second gripping member 369B is substantially L shaped, and the fixed second gripping member 368B has a shoulder formation in which the shorter arm of the L shape releasable second gripping member 369B can be received.

Figure 39:
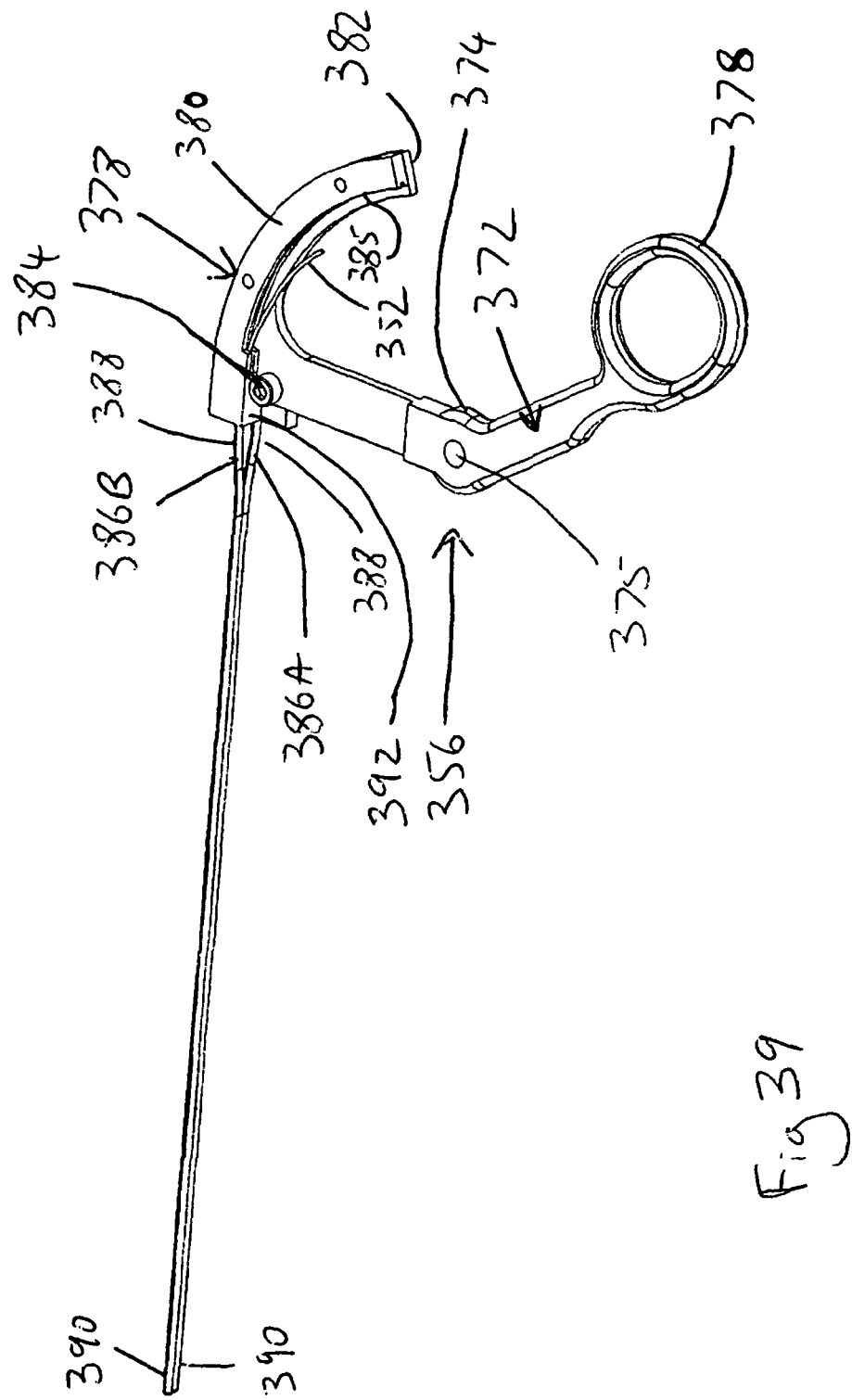
FIG. 39 is a side perspective view of a support arrangement for use in the delivery device shown in FIG. 35.

A second fastening member 370B in the form of a second screw is provided to fasten the releasable second gripping member 369B to the fixed second gripping member 368B. The second fastening member 370B extends through the releasable second gripping member 369B and is threadably received in a threaded hole (not shown) in the fixed second gripping member 3686. The second region of the elongate cutting wire 352 can be disposed between the fixed and releasable second gripping members 368B, 369B and gripped thereby upon tightening the second fastening member 370B thereon The support arrangement 356 is shown in FIG. 39 and comprises a support member 372 which has a central pivot region 374 defining a pivot aperture 375 at which the first and second delivery arrangements are pivotally mounted. The pivot member 359 extends through the pivot aperture 375.

A handle in the form of a support ring 376 is provided on the support member 372 on one side of the pivot region 374 and a guide arrangement 378 is provided on the support member 372 on the opposite side of the pivot region 374 to the support ring 376.

The delivery device 350 can be held by a user, who can insert a finger or thumb into the support ring 376 for that purpose.

Guide arrangement 378 comprises a concavely curved guide track 385 facing the support member 372. The guide arrangement 378 comprises two curved guide members 380, 382 attached to each other by bolts 384.

The guide arrangement 378 further includes first and second elongate guide tubes 386A, 386B. The first elongate guide tube 386B is provided to receive a region of the cutting wire 352 fed by the first delivery arrangement 354A. The second elongate guide tube 386B is provided to receive a region of the cutting wire 352 fed by the second delivery arrangement 354B.

Each of the first and second guide tubes 386A, 386B has a proximal end 388 and a distal end 390. The cutting wire 352 is urged by the first and second delivery arrangement 354A, 354B along the respective first and second guide tube 386A, 386B in a direction from the proximal end 388 to the distal end 390 of each guide tube 386A, 386B.

The first and second guide tubes 386A, 386B are held in a holding member 392 on the guide arrangement 378. The holding member 392 comprises a pair of three bores (not shown) into which the proximal ends 388 of each of the first and second guide tubes 386A, 386B are inserted.

In use, a single elongate cutting wire 352 is fed by hand into the first and second guide tubes 386A, 386B so that a first end region of the cutting wire 352 extends out of the proximal end 388 of the first guide tube 386A, and the second opposite end of the cutting wire 352 extends out of the proximal end 388 of the second guide tube 386B. The cutting wire 352 is fed into the first and second guide tubes 396A, 386B until only a short length (e.g. 2-4 mm) extends out of the distal ends 390 of the first and second guide tubes 386A, 386B. The first and second end regions of the cutting wire 352 are gripped by the first and second gripping arrangements 366A, 366B, with the first and second guide arrangements 354A, 354B pivoted to initial positions, shown in broken lines in FIG. 35. The user then inserts the elongate guide tubes 386A, 386B into one of the tunnels formed in the bone by the drilling steps described above until the proximal ends 390 of the first and second guide tubes 386A, 386B reach the cavity formed by the surgical apparatus 250. The surgeon then pulls the first guide arrangement 354A in the direction indicated by the arrow A in FIG. 35, which urges the first region of the elongate cutting wire 352 along the first guide tube 386A so that a short length thereof is pushed out of the distal end 390 of the first guide tube 386A.

The surgeon then moves the second delivery arrangement 354B in the direction indicated by arrow B, which urges the second region of the elongate cutting wire 352 along the second guide tube 386B so that a portion of the cutting wire 352 is pushed out of the distal end of the second elongate guide tube 386B. When the second delivery arrangement 354B is moved in the direction indicated by the arrow B, the guide member 378 ensures that the region of the cutting wire engaged in the guide track 385 is directed into the second elongate guide tube 386A, rather than simply bending under the force created by the movement of the second delivery arrangement 354A.

Thus, the region of the cutting element 352 that is urged out of the distal ends of the second guide tube 386B is pushed into the cavity formed by the surgical apparatus 250.

The next stage is for the surgeon to insert an elongate hook member into the other of the tunnels created by the drill on the opposite side of the implant and hook the curved region of the cutting wire in the cavity formed by the cavity forming member 250. The hook member is then retracted out of the tunnel in the bone pulling with it the cutting wire. The curved region of the cutting wire is then severed to provide two lengths of cutting wire in the bone.

Figure 40:
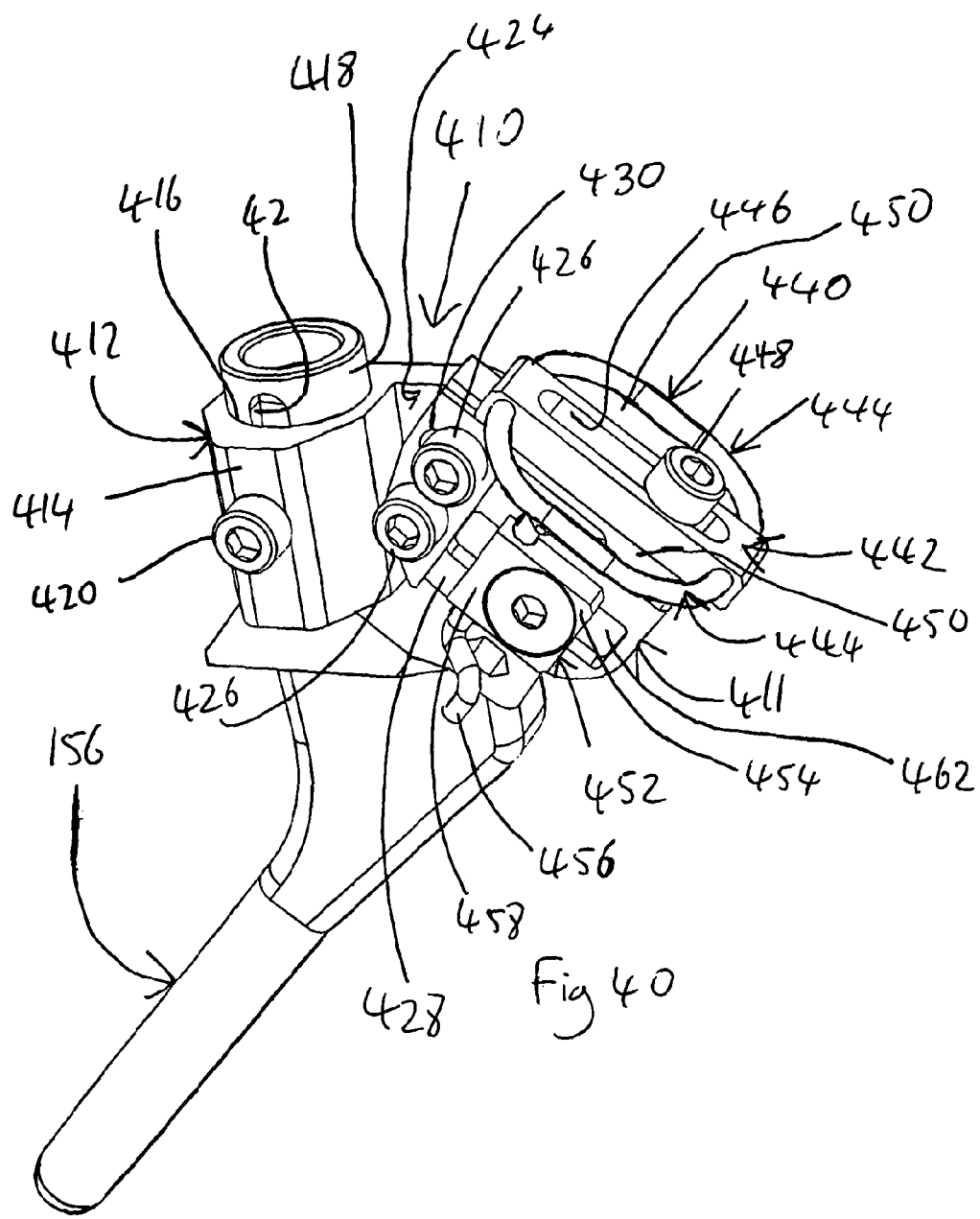
FIG. 40 is a perspective view from one side of a guide for an elongate cutter mounted upon an article.
Figure 41:
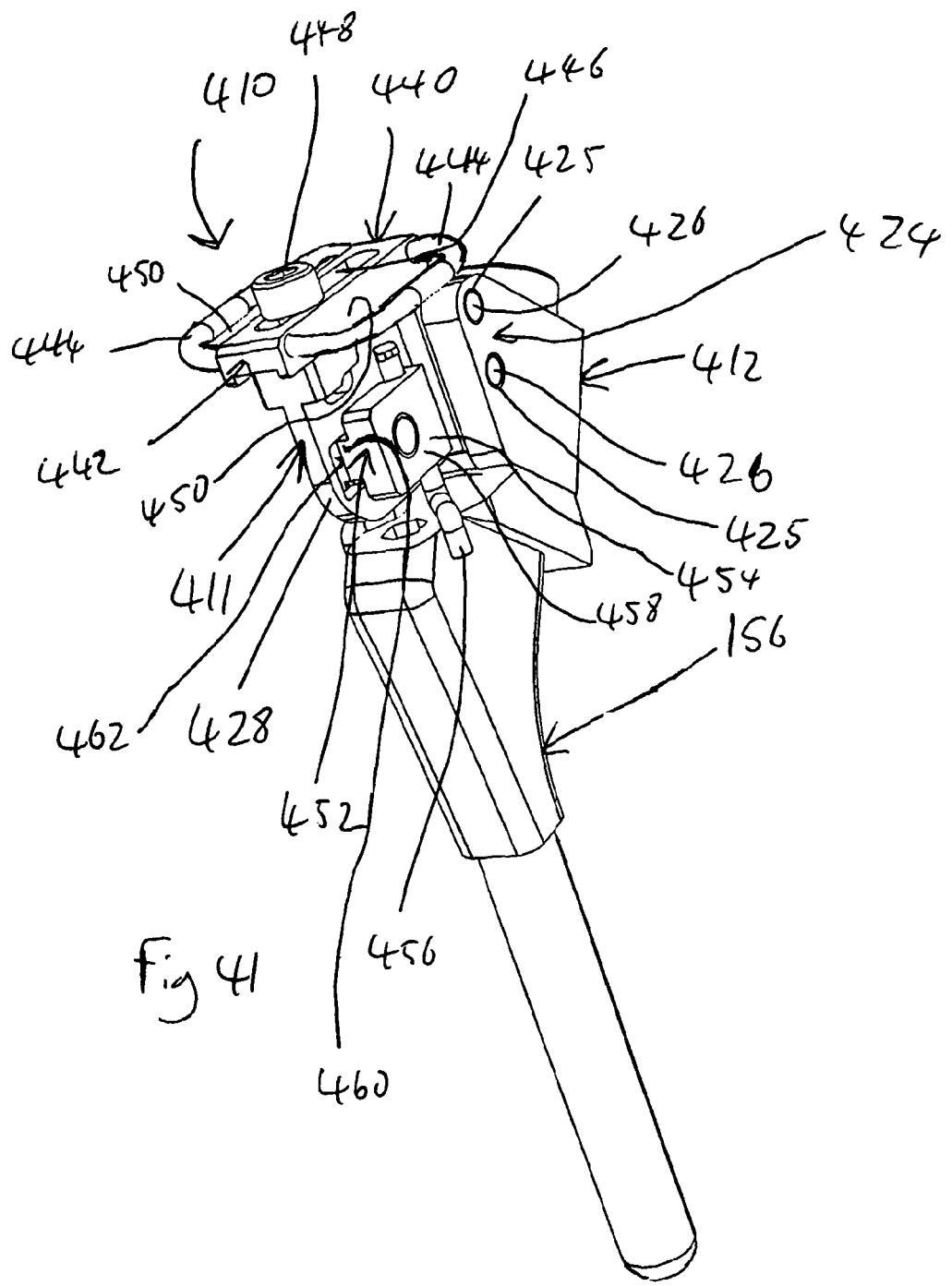
FIG. 41 is a perspective view from the opposite side of the guide shown in FIG. 40 on the article

FIGS. 40 and 41 show a guide for an elongate cutter, said guide being in the form of a wire guide 410 for guiding the elongate cutting wire 352 during the cutting of the bone, as explained below. The wire guide 410 is mounted on an implant 156, which is the same as the femoral implant 156 described above, having a projection 154, although the projection 154 is not visible in FIGS. 40 and 41.

The wire guide 410 comprises a mounting apparatus 412 for mounting the wire guide 410 on the projection 154 of the implant 156. The wire guide 410 further includes a support arrangement 411 to which the mounting apparatus 412 is attached.

The mounting apparatus 412 comprises a mounting member 414 which defines a bore 416 therethrough. The projection 154 on the implant 156 is received in the bore 416. A shim 418 is provided in the bore 416 between the inner surface of the bore 416 and the projection 154.

A bolt 420 is threadably received in a threaded aperture in the mounting member 414 and engages the projection 154 on the implant 156 to secure the mounting member 414 to the implant 156. The shim 418 defines a slot 422 through which the bolt 420 extends to engage the projection 154. The slot 422 allows adjustment of the position of the shim 418 relative to the mounting member 414.

An attaching member 424 extends from the mounting member 414 and is provided to attach the mounting apparatus 412 to the first holding member 172. The attaching member 424 defines a pair of threaded apertures 425 which can threadably receive bolts 426.

The support arrangement 411 comprises a support member 428 defining a pair of apertures 430, only one of which is visible in FIGS. 40 and 41. The bolts 426 extend through the apertures 430 in the support member 428 to be threadably received in respective threaded apertures 425 in the attaching member 424. The bolts 426 are tightened against the support member 428 to attach the mounting apparatus 412 to the support arrangement 411.

A guide assembly 440 is also attached to the support member 428. The guide assembly 440 comprises a carrier 442 and a pair of guide members 444 extending from the carrier 442 on opposite sides thereof. The carrier 442 defines a slot 446 through which a bolt 448 extends to be threadably received in a threaded aperture (not visible) in the support member 428. The slot 446 allows adjustment of the position of the guide assembly 440 on the support arrangement 411.

Each of the guide members 444 is in the form of an elongate element having opposite ends attached to the carrier 442. One end of each guide member 444 is attached to one end region of the carrier 442, and the opposite end of each guide member 444 is attached to the opposite end region of the carrier 442. A gap 450 is defined between the respective guide member 444 and the carrier 442. In use, as explained below, the cutting wire is threaded through the gaps 450 before cutting commences.

A locating assembly 52 is attached to the support member 428. The locating assembly 452 comprises a pair of clamping members 454 and a pair of locating members 456 clamped by the clamping members 454 to the support member 428.

Each clamping member 454 comprises a main portion 458 and a projecting portion 460. The support member 428 defines a through aperture 462, through which the projecting portion 460 of each clamping member 454 extends.

The locating members 456 are clamped to the support member 428 in a position such that they engage the implant 156 on opposite sides thereof. The locating members 456 thus prevent rotation of the wire guide 410 relative to the implant 156 during cutting with the cutting member.

In use, after the lengths of cutting wire 352, severed as described above, are threaded through the gaps 450 between the guide members 444 and the carrier 442.

The surgeon then attaches the ends of one of the lengths to suitable handles, and manipulates that length in a sawing action retracting the length of the cutting wire 352 up the bone thereby cutting the bone away from the implant. The wire guide constrains movement of the cutting wire 352 thereby ensuring that the cutting takes through the material directly adjacent the implant 156. When this has been done, the surgeon repeats the process with the other length of cutting wire 352 until the second length of cutting wire 352 is also pulled out of the bone using a sawing action. This results in the implant being freed from the bone and therefore allows the implant to be removed.

There is thus described various different apparatus that can be used in a method of removing an implant from a femur in a straight forward manner that causes minimal damage to the bone.

There is thus described a method and various apparatus for removing articles embedded in surrounding material, that quick and simple to effect or use, and involves minimal damage to the material.

The invention claimed is:

1. A drill guide for use in relation to removing implants from bones, the drill guide comprising a mounting arrangement for mounting the drill guide on the implant, first and second guide arrangements, wherein each of the first and second guide arrangements comprises a guide member through which a drill can be inserted, a holding arrangement for holding the first and second guide arrangements, the holding arrangement being adjustable between a release condition in which the positions of the first and second guide arrangements are adjustable relative to the holding arrangement and a holding condition in which the first and second guide arrangements are held by the holding arrangement in a fixed position, wherein each guide member comprises a body defining an aperture therethrough for receiving the drill; wherein the body is in the form of a tube, and the aperture is in the form of an elongate bore, and wherein each of the first and second guide arrangements further includes an adjustment member to allow adjustment of the position of the guide arrangement relative to the holding arrangement, wherein the adjustment member has a spheroidal configuration, and defines a hole therethrough, so that the drill can extend through the hole.

2. A drill guide according to claim 1, wherein the guide arrangements are pivotally adjustable relative to the holding arrangement.

3. A drill guide according to claim 1, wherein the adjustment member has an engagement face for engaging a part of the holding arrangement, with the engagement face being substantially planar.

4. A drill guide according to claim 1, wherein the holding arrangement comprises first and second holding members which are configured to engage the first and second guide arrangements therebetween.

5. A drill guide according to claim 4, wherein the first and second holding members engage the adjustment member of each of the first and second guide arrangements.

6. A drill guide according to claim 4, wherein each of the first and second holding members comprises a first region to engage the adjustment member of the first guide arrangement, and a second region to engage the adjustment member of the second guide arrangement.

7. A drill guide according to claim 6, wherein the adjustment members are sandwiched between the first and second holding members.

8. A drill guide according to claim 4, wherein the drill guide further includes tightening means to tighten the first and second holding members onto the adjustment members.

9. A drill guide according to claim 8, wherein the tightening means comprises: a first tightening member on the first holding member, the first tightening member extending through the second holding member; and a second tightening member co-operable with the first tightening member to urge the first and second holding members into the holding condition.

10. A drill guide according to claim 9, wherein the second tightening member engages the second holding member when co-operating with the first tightening member to urge the first and second holding members tightly onto the adjustment members.

11. A drill guide according to claim 10, wherein the first and second tightening members are threaded so that the first and second tightening members can be screwed onto each other.

12. A drill guide according to claim 4, wherein each of the first and second guide arrangements includes a securing means to secure the guide arrangement to the holding arrangement.

13. A drill guide according to claim 12, wherein the securing means comprises a securing portion secured to the holding arrangement, the securing portion defining a slot, and wherein the drill guide further includes a fastening member extending through the slot to secure the securing portion to the holding arrangement.

14. A drill guide according to claim 13, wherein the securing means comprises a connecting portion to connect the securing portion to the guide member.

15. A drill guide according to claim 4, including a securing member on one of the first and second holding members, wherein the fastening member co-operates with the securing member to secure the first and second guide arrangements thereto.

16. A drill guide according to claim 15, wherein the fastening member extends through the securing portions of each of the first and second guide arrangements to co-operate with the securing member on the first or second holding member.

17. A drill guide according to claim 16, wherein the securing member is elongate and extends from the second holding member.

18. A drill guide according to claim 4, wherein the holding arrangement comprises an attaching means to attach the holding arrangement to the mounting arrangement, the attaching means comprising an attaching member which extends transverse from the first or second holding member.

19. A drill guide according to claim 18, wherein the attaching member defines at least one slot through which at least one fastening element can extend to co-operate with at least one corresponding aperture in the mounting arrangement.

20. A drill guide according to claim 18, wherein the mounting arrangement comprises a mounting member defining a bore through which a projection on the mount can be received.

21. A drill guide according to claim 20, wherein the mounting arrangement further includes a fastening element which can be received in an aperture defined in the mounting member to extend to the bore in the mounting member.

22. A drill guide according to claim 20, wherein the mounting member defines attaching apertures to which the fastening members on the attaching means can be threadably received.

23. A drill guide for use in relation to removing implants from bones, the drill guide comprising a mounting arrangement for mounting the drill guide on the implant, first and second guide arrangements, a holding arrangement for holding the first and second guide arrangements, the holding arrangement being adjustable between a release condition in which the positions of the first and second guide arrangements are adjustable relative to the holding arrangement and a holding condition in which the first and second guide arrangements are held by the holding arrangement in a fixed position;

wherein each of the first and second guide arrangements comprises a guide member through which a drill can be inserted;

wherein the guide member comprises a body defining an aperture therethrough for receiving the drill;

wherein each of the first and second guide arrangements further includes an adjustment member to allow adjustment of the position of the guide arrangement relative to the holding arrangement, and the adjustment member comprises a member having a curved surface;

wherein the holding arrangement comprises first and second holding members which are configured to engage the first and second guide arrangements therebetween; and wherein each of the first and second holding members is generally H shaped.

24. A drill guide for use in relation to removing implants from bones, the drill guide comprising a mounting arrangement for mounting the drill guide on the implant, first and second guide arrangements, a holding arrangement for holding the first and second guide arrangements, the holding arrangement being adjustable between a release condition in which the positions of the first and second guide arrangements are adjustable relative to the holding arrangement and a holding condition in which the first and second guide arrangements are held by the holding arrangement in a fixed position;

wherein each of the first and second guide arrangements comprises a guide member through which a drill can be inserted;

wherein the guide member comprises a body defining an aperture therethrough for receiving the drill;

wherein each of the first and second guide arrangements further includes an adjustment member to allow adjustment of the position of the guide arrangement relative to the holding arrangement, and the adjustment member comprises a member having a curved surface;

wherein the holding arrangement comprises first and second holding members which are configured to engage the first and second guide arrangements therebetween;

wherein each of the first and second guide arrangements includes a securing means to secure the guide arrangement to the holding arrangement;

wherein the securing means comprises a securing portion secured to the holding arrangement, the securing portion defining a slot, and wherein the drill guide further includes a fastening member extending through the slot to secure the securing portion to the holding arrangement; and wherein the securing portion of one of the first and second guide arrangements overlaps the securing portion of the other of the first and second guide arrangements, and a fastening member extends through the slots of the securing portions of each of the first and second guide arrangements.

25. A drill guide for use in relation to removing implants from bones, the drill guide comprising a mounting arrangement for mounting the drill guide on the implant, first and second guide arrangements, a holding arrangement for holding the first and second guide arrangements, the holding arrangement being adjustable between a release condition in which the positions of the first and second guide arrangements are adjustable relative to the holding arrangement and a holding condition in which the first and second guide arrangements are held by the holding arrangement in a fixed position;

wherein each of the first and second guide arrangements comprises a guide member through which a drill can be inserted;

wherein the guide member comprises a body defining an aperture therethrough for receiving the drill;

wherein each of the first and second guide arrangements further includes an adjustment member to allow adjustment of the position of the guide arrangement relative to the holding arrangement, and the adjustment member comprises a member having a curved surface;

wherein the holding arrangement comprises first and second holding members which are configured to engage the first and second guide arrangements therebetween;

wherein the holding arrangement comprises an attaching means to attach the holding arrangement to the mounting arrangement, the attaching means comprising an attaching member which extends transverse from the first or second holding member;

wherein the mounting arrangement comprises a mounting member defining a bore through which a projection on the mount can be received; and wherein the mounting arrangement further includes a shim member arranged in the bore in the mounting member, the shim member defining a slot through which the fastening member can be received to engage the projection on the mount.

* * * * *